(12) United States Patent
Akiyama et al.

(10) Patent No.: US 7,422,906 B2
(45) Date of Patent: Sep. 9, 2008

(54) APOPTOSIS-INDUCING GENE AND UTILIZATION OF THE SAME

(75) Inventors: Tetsu Akiyama, 1493-1-604, Kaidori, Tama-shi, Tokyo 206-0012 (JP); Takatoshi Hiroko, Tokyo (JP)

(73) Assignees: Taisho Pharmaceutical Co., Ltd., Tokyo (JP); Tetsu Akiyama, Tokyo (JP)

( * ) Notice: Subject to any disclaimer, the term of this patent is extended or adjusted under 35 U.S.C. 154(b) by 0 days.

(21) Appl. No.: 10/544,809

(22) PCT Filed: Feb. 10, 2004

(86) PCT No.: PCT/JP2004/001424
§ 371 (c)(1), (2), (4) Date: Feb. 16, 2006

(87) PCT Pub. No.: WO2004/069869
PCT Pub. Date: Aug. 19, 2004

(65) Prior Publication Data
US 2006/0172930 A1 Aug. 3, 2006

(30) Foreign Application Priority Data
Feb. 10, 2003 (JP) ............................. 2003-032036

(51) Int. Cl.
*C12P 21/06* (2006.01)
*C07K 14/00* (2006.01)
(52) U.S. Cl. .................................. 436/69.1; 530/350
(58) Field of Classification Search ........................ None
See application file for complete search history.

(56) References Cited

U.S. PATENT DOCUMENTS
2007/0020637 A1 * 1/2007 Isogai et al. .................. 435/6

FOREIGN PATENT DOCUMENTS
WO 01/81363 11/2001

OTHER PUBLICATIONS

OM protein—protein search, using sw model Run on: Jul. 11, 2007, pp. 1-4.*
Collins et al., Generation and initial analysis of more than 15,000 full-length human and mouse cDNA sequences, Proc Natl Acad Sci USA, Dec. 24, 2002; vol. 99, No. 16899-16903.*
Duvall and Wyllie, Immunology Today, 7 (4), 115-119 (1986).
Nagata, S., (1998), Jikken Igaku (Experimental Medicine), vol. 16, 1242-1246.
Nagata, S., (1997) Cell, 88, 355-365.
Haldar, S., et al., (1995) Proc. Natl. Acad. Sci. USA 92, 4507-4511.

* cited by examiner

*Primary Examiner*—Robert B. Mondesi
(74) *Attorney, Agent, or Firm*—Greenblum & Bernstein, P.L.C.

(57) ABSTRACT

The object of the present invention is to provide a protein useful for searching an apoptosis-inhibiting substance or an apoptosis-promoting substance, a gene encoding the above protein, a vector comprising the above gene, and a transformant comprising the above vector. The present invention provides an apoptosis-inducing protein of any one of the following (a), (b), and (c):

(a) a protein having the amino acid sequence shown in SEQ ID NO: 2 of the sequence listing;
(b) a protein, which has an amino acid sequence comprising a deletion, substitution, and/or addition of one or several amino acids with respect to the amino acid sequence shown in SEQ ID NO: 2 of the sequence listing, and has activity of inducing apoptosis; and
(c) a protein, which has an amino acid sequence showing homology of 95% or more with the amino acid sequence shown in SEQ ID NO: 2 of the sequence listing, and has activity of inducing apoptosis.

3 Claims, 10 Drawing Sheets

Fig. 3

KH domain 1

```
D8                      VPVPSSEHVAEIVGRQGCKIKALRAKTNTYIKTPVRGEEPVFVVTGRKEDVAMARREIISAAEHFS
D8C1                    VPVPTSEHVAEIVGRQGCKIKALRAKTNTYIKTPVRGEEPVFMVTGRREDVATARREIISAAEHFS
D8C18                   SAGTTQLSPSTACHPKGCKIKALRAKTNTYIKTPVRGEEPIFVVTGRKEDVAMAKREILSAAEHFS
D8C19                   VPVPSSEHVAEIVGRQGCKIKALRAKTNTYIKTPVRGEEPVFIVTGRKEDVEMAKREILSAAEHFS
C.elegans MEX-3         VEVPTSEHVAEIVGRQGCKIKALRAKTNTYIKTPVRGEDPIFVVTGRLEDVNEAKREIDCAAEHPT
Ciona savignyl pem-3    VPVPSSEHVAEIVGRQGCKIKALRAKTNTYIKTPVRGEEPVFVVTGRKEDVAMARREVQSAAEHFT
D.melanogaster CG11360                   CKIKALRAKINTYIKTPVRGEEPVFVVTGRKEDVNKAKREILSAADHFS
```

KH domain 2

```
D8                      RVPYRVVGLVVGPKGATIKRIQQQTHTYIVTPSRDKEPVFEVTGMPENVDRAREEIEAHIALRT
D8C1                    RVPYRVVGLVVGPKGATIKRIQQQTNTYIITPSRDRDPVFEITGAPGNVBRAREEIETHIAVRT
D8C18                   RVPIRVVGLVVGPKGATIKRIQQQTNTYIVTPSRDKEPVFEVTGMPENVDRAREEIEMHIAMRT
D8C19                   RVPIRVVGLVVGPKGATIKRIQQRTHTYIVTPGRDKEPVFAVTGMPENVDRAREEIEAMITLRT
C.elegans MEX-3         RVPLRVVGLVVGPKGATIKRIQQDTHTYIITPSRERBPVFEVTGLPHNVEAARKEIBTHIFQRT
Ciona savignyl pem-3    RVPIRVVGLVVGPKGATIKRIQQDTHTYIVTPSRDKEPVFEVTGLPENVEKAKEEIBAHIATRT
D.melanogaster CG11360  RVPYRVVGLVVGPKGATIKHIQQETQTYIVTPSREKBPIFEVTGLPDNVDTARKQIEAHIALRT
```

RING finger

```
D8                      DCSVCFESEVIAALVPCGHNLFCMECANRICEKSEPECPVCH
D8C1                    DCMVCFESEVTAALVPCGHNLFCMECAVRICERTDPECPVCH
D8C18                   DCVICFENEVIAALVPCGHNLFCMECANKICEKRTPSCPVCQ
D8C19                   BCVVCAEGEVMAALVPCGHNLFCMDCAVRICGKSEPECPACR
Ciona savignyl pem-3    RCTLCNDGSVVATLMPCRHQVFCFPCANRVVSRSASFCPYCH
D.melanogaster CG11360  BCFVCNENTVTTALVPCGHNMFCMECANHICLSMDAVCPVCN
```

Fig. 5
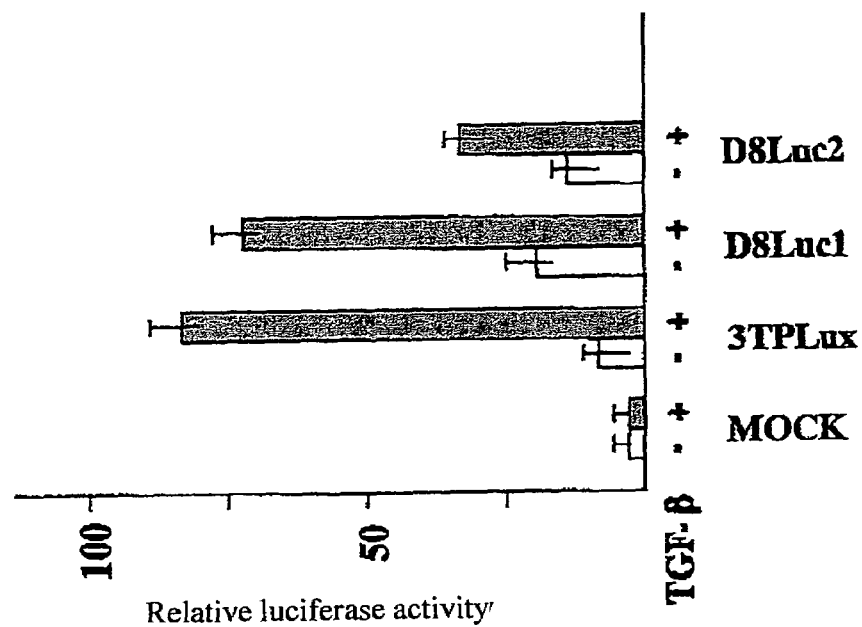
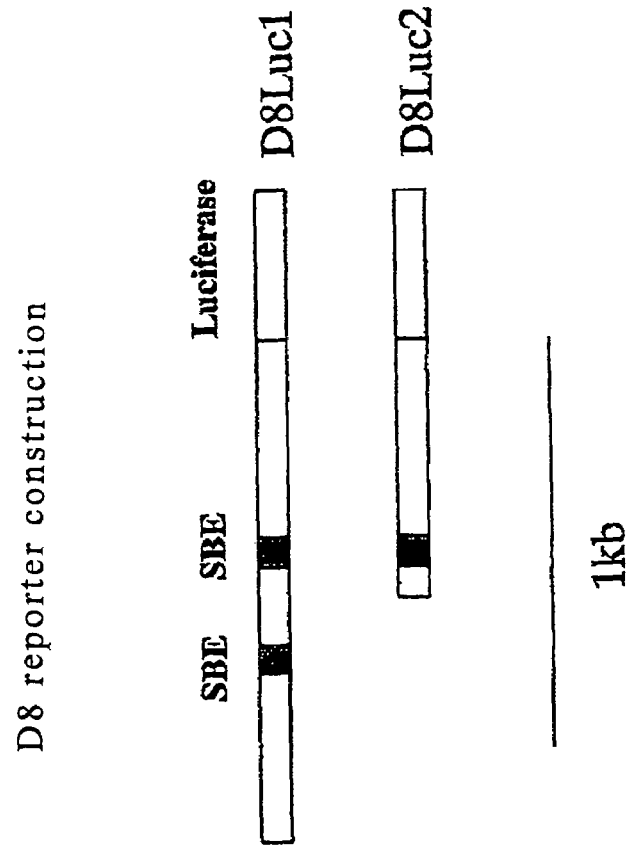

Fig. 6
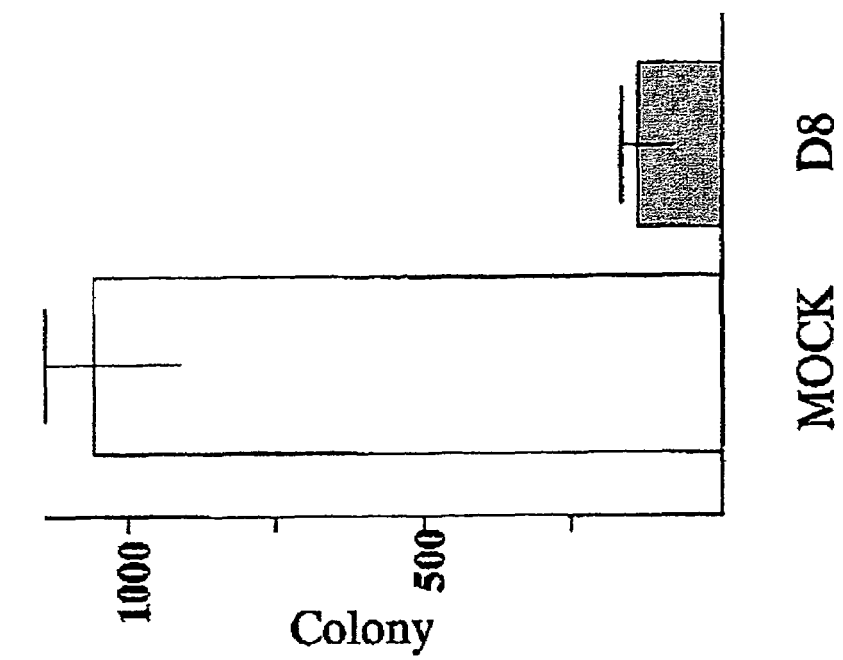
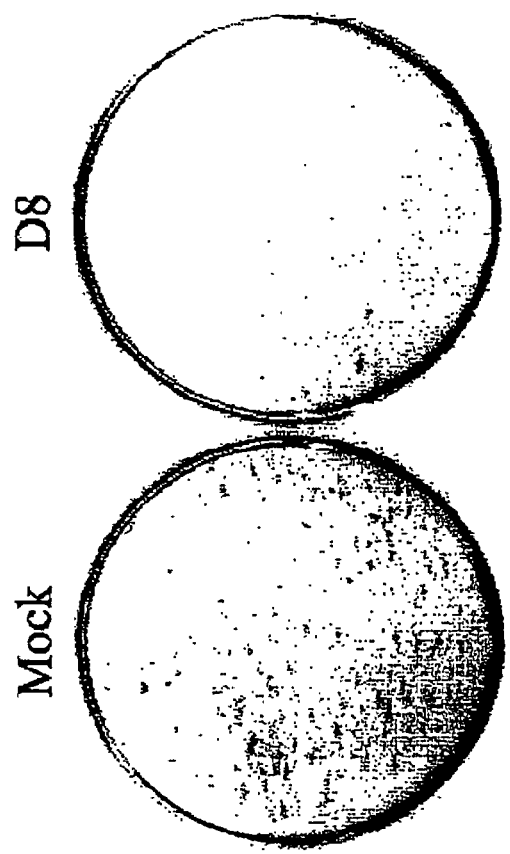
Colony formation assay

SEQUENCE LISTING

```
<160> NUMBER OF SEQ ID NOS: 33

<210> SEQ ID NO 1
<211> LENGTH: 1710
<212> TYPE: DNA
<213> ORGANISM: Homo sapiens
<220> FEATURE:
<221> NAME/KEY: CDS
<222> LOCATION: (1)..(1707)

<400> SEQUENCE: 1
```

-continued

```
atg ccc agc tcg ctg ttc gca gac ctg gag cgc aac ggc agc ggc ggc    48
Met Pro Ser Ser Leu Phe Ala Asp Leu Glu Arg Asn Gly Ser Gly Gly
 1               5                  10                  15 ggc ggc ggc ggc agc agc gga ggg gga gag acc ctg gat gac caa aga    96
Gly Gly Gly Gly Ser Ser Gly Gly Gly Glu Thr Leu Asp Asp Gln Arg
             20                  25                  30 gcc ctg cag ctc gcg ctc gac cag ctc tcc ctg ctg ggg ctg gac agt   144
Ala Leu Gln Leu Ala Leu Asp Gln Leu Ser Leu Leu Gly Leu Asp Ser
         35                  40                  45 gac gag ggc gcc tct ctg tac gac agc gag ccg cgc aag aag agc gtg   192
Asp Glu Gly Ala Ser Leu Tyr Asp Ser Glu Pro Arg Lys Lys Ser Val
 50                  55                  60 aac atg acc gag tgc gtg cca gta ccc agt tct gag cat gtc gcc gag   240
Asn Met Thr Glu Cys Val Pro Val Pro Ser Ser Glu His Val Ala Glu
 65                  70                  75                  80 atc gtg ggg cgg caa ggt tgt aaa atc aaa gcg ctg cgg gcg aag acc   288
Ile Val Gly Arg Gln Gly Cys Lys Ile Lys Ala Leu Arg Ala Lys Thr
             85                  90                  95 aat act tac atc aag acc cca gtt cgc ggg gag gag cct gtc ttt gtt   336
Asn Thr Tyr Ile Lys Thr Pro Val Arg Gly Glu Glu Pro Val Phe Val
            100                 105                 110 gtg acg ggc agg aag gag gat gtg gcc atg gct cgg agg gag atc atc   384
Val Thr Gly Arg Lys Glu Asp Val Ala Met Ala Arg Arg Glu Ile Ile
        115                 120                 125 tct gct gcc gag cac ttc tcc atg atc cgc gcc tcc cgg aat aag aac   432
Ser Ala Ala Glu His Phe Ser Met Ile Arg Ala Ser Arg Asn Lys Asn
130                 135                 140 acg gca ctc aac ggc gcg gtg cct ggg ccg ccc aac ctg ccc ggg cag   480
Thr Ala Leu Asn Gly Ala Val Pro Gly Pro Pro Asn Leu Pro Gly Gln
145                 150                 155                 160 acc acc atc caa gtg cgg gta ccc tac cgc gtg gtg ggg ctc gtg gtg   528
Thr Thr Ile Gln Val Arg Val Pro Tyr Arg Val Val Gly Leu Val Val
                165                 170                 175 ggg ccc aaa ggc gcc aca atc aag cgc atc cag cag cag acg cac acg   576
Gly Pro Lys Gly Ala Thr Ile Lys Arg Ile Gln Gln Gln Thr His Thr
            180                 185                 190 tac atc gtg acg ccc agc cgg gat aag gag ccg gtg ttc gag gtg acc   624
Tyr Ile Val Thr Pro Ser Arg Asp Lys Glu Pro Val Phe Glu Val Thr
        195                 200                 205 ggc atg cca gag aac gtg gat cgc gct cga gag gag att gag gcg cac   672
Gly Met Pro Glu Asn Val Asp Arg Ala Arg Glu Glu Ile Glu Ala His
    210                 215                 220 att gct ctg cgt acc ggc ggc atc att gag ctc aca gac gag aac gac   720
Ile Ala Leu Arg Thr Gly Gly Ile Ile Glu Leu Thr Asp Glu Asn Asp
225                 230                 235                 240 ttc cac gcc aac ggc acc gat gtg ggc ttc gat ctg cat cat ggg tcc   768
Phe His Ala Asn Gly Thr Asp Val Gly Phe Asp Leu His His Gly Ser
                245                 250                 255 ggc ggg tcc ggc cca ggc agc ctc tgg agc aag ccc acc ccc agc atc   816
Gly Gly Ser Gly Pro Gly Ser Leu Trp Ser Lys Pro Thr Pro Ser Ile
            260                 265                 270 acg ccc acc ccc ggc cgc aag cct ttc tct agc tac cgc aac gac agc   864
Thr Pro Thr Pro Gly Arg Lys Pro Phe Ser Ser Tyr Arg Asn Asp Ser
        275                 280                 285 tcc agc tcg ctt ggc agt gct tcc aca gac tct tat ttc ggc ggc ggg   912
Ser Ser Ser Leu Gly Ser Ala Ser Thr Asp Ser Tyr Phe Gly Gly Gly
    290                 295                 300 acc agc agc agc gca gcg gct acc cag cgc ctg gcg gac tac agc ccc   960
Thr Ser Ser Ser Ala Ala Ala Thr Gln Arg Leu Ala Asp Tyr Ser Pro
```

-continued

| | | | |
|---|---|---|---|
| 305 | 310 | 315 | 320 | cct agc ccc gcc ctg agc ttt gcg cac aac gga aac aat aac aat aac    1008
Pro Ser Pro Ala Leu Ser Phe Ala His Asn Gly Asn Asn Asn Asn Asn
                325                 330                 335 ggc aat ggg tac acc tac aca gcg ggg gga gaa gcc tca gtg cca tcc    1056
Gly Asn Gly Tyr Thr Tyr Thr Ala Gly Gly Glu Ala Ser Val Pro Ser
                340                 345                 350 ccc gac ggc tgc ccc gag ctg cag ccc act ttt gac ccg gct ccc gct    1104
Pro Asp Gly Cys Pro Glu Leu Gln Pro Thr Phe Asp Pro Ala Pro Ala
            355                 360                 365 ccc cca cct ggg gca cca ctt atc tgg gcc cag ttc gag cgg tcc ccg    1152
Pro Pro Pro Gly Ala Pro Leu Ile Trp Ala Gln Phe Glu Arg Ser Pro
        370                 375                 380 gga ggc gga cct gca gct ccg gta tct tct tcc tgc tct tct tct gca    1200
Gly Gly Gly Pro Ala Ala Pro Val Ser Ser Ser Cys Ser Ser Ser Ala
385                 390                 395                 400 tct tcg tct gct tct tcc tcc tcc gtg gtc ttc ccc ggg ggt ggc gcc    1248
Ser Ser Ser Ala Ser Ser Ser Ser Val Val Phe Pro Gly Gly Gly Ala
                405                 410                 415 agt gcg ccc tcc aac gcc aac ctg ggg cta ttg gtg cac cgc cgg ctg    1296
Ser Ala Pro Ser Asn Ala Asn Leu Gly Leu Leu Val His Arg Arg Leu
                420                 425                 430 cac cct ggc acc agc tgc ccg cgc ctg tct cca ccc ttg cac atg gcc    1344
His Pro Gly Thr Ser Cys Pro Arg Leu Ser Pro Pro Leu His Met Ala
            435                 440                 445 ccg ggg gcg gga gag cac cac ctg gct cgc cgg gtg cgc agc gac ccg    1392
Pro Gly Ala Gly Glu His His Leu Ala Arg Arg Val Arg Ser Asp Pro
        450                 455                 460 ggt gga gga ggc ctg gcc tac gcc gct tat gcc aac ggg ctg ggg gca    1440
Gly Gly Gly Gly Leu Ala Tyr Ala Ala Tyr Ala Asn Gly Leu Gly Ala
465                 470                 475                 480 cag ctg cct ggc ttg cag ccg tcg gac acg tcg ggc tcc tcc tct tcg    1488
Gln Leu Pro Gly Leu Gln Pro Ser Asp Thr Ser Gly Ser Ser Ser Ser
                485                 490                 495 tcc agc tcc tcc tcc agc tct tca tcc tct tcc tcc ggg ctt cgg cgt    1536
Ser Ser Ser Ser Ser Ser Ser Ser Ser Ser Ser Gly Leu Arg Arg
                500                 505                 510 aaa ggc agc cgc gac tgc tcc gtg tgc ttc gag agc gaa gtg att gcc    1584
Lys Gly Ser Arg Asp Cys Ser Val Cys Phe Glu Ser Glu Val Ile Ala
                515                 520                 525 gcg ctg gtg ccc tgt ggc cac aac ctc ttc tgc atg gag tgc gcc aat    1632
Ala Leu Val Pro Cys Gly His Asn Leu Phe Cys Met Glu Cys Ala Asn
            530                 535                 540 cgc atc tgt gag aag agc gag ccc gag tgc ccg gtc tgc cac acc gcg    1680
Arg Ile Cys Glu Lys Ser Glu Pro Glu Cys Pro Val Cys His Thr Ala
545                 550                 555                 560 gtc act cag gcc atc cgc atc ttt tct taa                            1710
Val Thr Gln Ala Ile Arg Ile Phe Ser
                565

<210> SEQ ID NO 2
<211> LENGTH: 569
<212> TYPE: PRT
<213> ORGANISM: Homo sapiens

<400> SEQUENCE: 2

Met Pro Ser Ser Leu Phe Ala Asp Leu Glu Arg Asn Gly Ser Gly Gly
  1               5                  10                  15

Gly Gly Gly Gly Ser Ser Gly Gly Glu Thr Leu Asp Asp Gln Arg
             20                  25                  30

```
Ala Leu Gln Leu Ala Leu Asp Gln Leu Ser Leu Gly Leu Asp Ser
         35                  40                  45

Asp Glu Gly Ala Ser Leu Tyr Asp Ser Glu Pro Arg Lys Lys Ser Val
         50                  55                  60

Asn Met Thr Glu Cys Val Pro Val Pro Ser Ser Glu His Val Ala Glu
 65                  70                  75                  80

Ile Val Gly Arg Gln Gly Cys Lys Ile Lys Ala Leu Arg Ala Lys Thr
                 85                  90                  95

Asn Thr Tyr Ile Lys Thr Pro Val Arg Gly Glu Pro Val Phe Val
                100                 105                 110

Val Thr Gly Arg Lys Glu Asp Val Ala Met Ala Arg Glu Ile Ile
             115                 120                 125

Ser Ala Ala Glu His Phe Ser Met Ile Arg Ala Ser Arg Asn Lys Asn
         130                 135                 140

Thr Ala Leu Asn Gly Ala Val Pro Gly Pro Pro Asn Leu Pro Gly Gln
145                 150                 155                 160

Thr Thr Ile Gln Val Arg Val Pro Tyr Arg Val Val Gly Leu Val Val
                165                 170                 175

Gly Pro Lys Gly Ala Thr Ile Lys Arg Ile Gln Gln Gln Thr His Thr
                180                 185                 190

Tyr Ile Val Thr Pro Ser Arg Asp Lys Glu Pro Val Phe Glu Val Thr
            195                 200                 205

Gly Met Pro Glu Asn Val Asp Arg Ala Arg Glu Glu Ile Glu Ala His
            210                 215                 220

Ile Ala Leu Arg Thr Gly Gly Ile Ile Glu Leu Thr Asp Glu Asn Asp
225                 230                 235                 240

Phe His Ala Asn Gly Thr Asp Val Gly Phe Asp Leu His Gly Ser
                245                 250                 255

Gly Gly Ser Gly Pro Gly Ser Leu Trp Ser Lys Pro Thr Pro Ser Ile
            260                 265                 270

Thr Pro Thr Pro Gly Arg Lys Pro Phe Ser Ser Tyr Arg Asn Asp Ser
            275                 280                 285

Ser Ser Ser Leu Gly Ser Ala Ser Thr Asp Ser Tyr Phe Gly Gly Gly
            290                 295                 300

Thr Ser Ser Ser Ala Ala Ala Thr Gln Arg Leu Ala Asp Tyr Ser Pro
305                 310                 315                 320

Pro Ser Pro Ala Leu Ser Phe Ala His Asn Gly Asn Asn Asn Asn
                325                 330                 335

Gly Asn Gly Tyr Thr Tyr Thr Ala Gly Gly Glu Ala Ser Val Pro Ser
            340                 345                 350

Pro Asp Gly Cys Pro Glu Leu Gln Pro Thr Phe Asp Pro Ala Pro Ala
            355                 360                 365

Pro Pro Pro Gly Ala Pro Leu Ile Trp Ala Gln Phe Glu Arg Ser Pro
            370                 375                 380

Gly Gly Gly Pro Ala Ala Pro Val Ser Ser Ser Cys Ser Ser Ser Ala
385                 390                 395                 400

Ser Ser Ser Ala Ser Ser Ser Val Val Phe Pro Gly Gly Gly Ala
                405                 410                 415

Ser Ala Pro Ser Asn Ala Asn Leu Gly Leu Leu Val His Arg Arg Leu
            420                 425                 430

His Pro Gly Thr Ser Cys Pro Arg Leu Ser Pro Pro Leu His Met Ala
            435                 440                 445
```

-continued

```
Pro Gly Ala Gly Glu His His Leu Ala Arg Arg Val Arg Ser Asp Pro
    450                 455                 460
Gly Gly Gly Gly Leu Ala Tyr Ala Ala Tyr Ala Asn Gly Leu Gly Ala
465                 470                 475                 480
Gln Leu Pro Gly Leu Gln Pro Ser Asp Thr Ser Gly Ser Ser Ser Ser
                485                 490                 495
Ser Ser Ser Ser Ser Ser Ser Ser Ser Ser Ser Gly Leu Arg Arg
            500                 505                 510
Lys Gly Ser Arg Asp Cys Ser Val Cys Phe Glu Ser Glu Val Ile Ala
        515                 520                 525
Ala Leu Val Pro Cys Gly His Asn Leu Phe Cys Met Glu Cys Ala Asn
    530                 535                 540
Arg Ile Cys Glu Lys Ser Glu Pro Glu Cys Pro Val Cys His Thr Ala
545                 550                 555                 560
Val Thr Gln Ala Ile Arg Ile Phe Ser
                565
```

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
tatagaattc atgcccagct cgctgttcgc                                       30

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tatagtcgac ttaagaaaag atgcggatgg                                       30

<210> SEQ ID NO 5
<211> LENGTH: 73
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
acatgctcag aactgggtac tggcacgcga agcttggcgt gccagtaccc agttctgagc      60
atgtcgcttt ttt                                                         73

<210> SEQ ID NO 6
<211> LENGTH: 79
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gatcaaaaaa gcgacatgct cagaactggg tactggcacg ccaagcttcg cgtgccagta      60
cccagttctg agcatgtcg                                                   79

<210> SEQ ID NO 7
<211> LENGTH: 66
<212> TYPE: PRT
<213> ORGANISM: Homo sapiens

<400> SEQUENCE: 7

Val Pro Val Pro Ser Ser Glu His Val Ala Glu Ile Val Gly Arg Gln
 1               5                  10                  15

Gly Cys Lys Ile Lys Ala Leu Arg Ala Lys Thr Asn Thr Tyr Ile Lys
                20                  25                  30

Thr Pro Val Arg Gly Glu Glu Pro Val Phe Val Val Thr Gly Arg Lys
            35                  40                  45

Glu Asp Val Ala Met Ala Arg Arg Glu Ile Ile Ser Ala Ala Glu His
        50                  55                  60

Phe Ser
 65

<210> SEQ ID NO 8
<211> LENGTH: 66
<212> TYPE: PRT
<213> ORGANISM: Homo sapiens

<400> SEQUENCE: 8

Val Pro Val Pro Thr Ser Glu His Val Ala Glu Ile Val Gly Arg Gln
 1               5                  10                  15

Gly Cys Lys Ile Lys Ala Leu Arg Ala Lys Thr Asn Thr Tyr Ile Lys
                20                  25                  30

Thr Pro Val Arg Gly Glu Glu Pro Val Phe Met Val Thr Gly Arg Arg
            35                  40                  45

Glu Asp Val Ala Thr Ala Arg Arg Glu Ile Ile Ser Ala Ala Glu His
        50                  55                  60

Phe Ser
 65

<210> SEQ ID NO 9
<211> LENGTH: 66
<212> TYPE: PRT
<213> ORGANISM: Homo sapiens

<400> SEQUENCE: 9

Ser Ala Gly Thr Thr Gln Leu Ser Pro Ser Thr Ala Cys His Pro Lys
 1               5                  10                  15

Gly Cys Lys Ile Lys Ala Leu Arg Ala Lys Thr Asn Thr Tyr Ile Lys
                20                  25                  30

Thr Pro Val Arg Gly Glu Glu Pro Ile Phe Val Val Thr Gly Arg Lys
            35                  40                  45

Glu Asp Val Ala Met Ala Lys Arg Glu Ile Leu Ser Ala Ala Glu His
        50                  55                  60

Phe Ser
 65

<210> SEQ ID NO 10
<211> LENGTH: 66
<212> TYPE: PRT
<213> ORGANISM: Homo sapiens

<400> SEQUENCE: 10

Val Pro Val Pro Ser Ser Glu His Val Ala Glu Ile Val Gly Arg Gln

```
                1               5                  10                 15
Gly Cys Lys Ile Lys Ala Leu Arg Ala Lys Thr Asn Thr Tyr Ile Lys
                    20                  25                  30

Thr Pro Val Arg Gly Glu Glu Pro Val Phe Ile Val Thr Gly Arg Lys
            35                  40                  45

Glu Asp Val Glu Met Ala Lys Arg Glu Ile Leu Ser Ala Ala Glu His
        50                  55                  60

Phe Ser
 65

<210> SEQ ID NO 11
<211> LENGTH: 66
<212> TYPE: PRT
<213> ORGANISM: Caenorhabditis elegans

<400> SEQUENCE: 11

Val Glu Val Pro Thr Ser Glu His Val Ala Glu Ile Val Gly Arg Gln
 1               5                  10                  15

Gly Cys Lys Ile Lys Ala Leu Arg Ala Lys Thr Asn Thr Tyr Ile Lys
                    20                  25                  30

Thr Pro Val Arg Gly Glu Asp Pro Ile Phe Val Val Thr Gly Arg Leu
            35                  40                  45

Glu Asp Val Asn Glu Ala Lys Arg Glu Ile Asp Cys Ala Ala Glu His
        50                  55                  60

Phe Thr
 65

<210> SEQ ID NO 12
<211> LENGTH: 66
<212> TYPE: PRT
<213> ORGANISM: Ciona savignyi

<400> SEQUENCE: 12

Val Pro Val Pro Ser Ser Glu His Val Ala Glu Ile Val Gly Arg Gln
 1               5                  10                  15

Gly Cys Lys Ile Lys Ala Leu Arg Ala Lys Thr Asn Thr Tyr Ile Lys
                    20                  25                  30

Thr Pro Val Arg Gly Glu Glu Pro Val Phe Val Val Thr Gly Arg Lys
            35                  40                  45

Glu Asp Val Ala Met Ala Arg Arg Glu Val Gln Ser Ala Ala Glu His
        50                  55                  60

Phe Thr
 65

<210> SEQ ID NO 13
<211> LENGTH: 49
<212> TYPE: PRT
<213> ORGANISM: Drosophila melanogaster

<400> SEQUENCE: 13

Cys Lys Ile Lys Ala Leu Arg Ala Lys Thr Asn Thr Tyr Ile Lys Thr
 1               5                  10                  15

Pro Val Arg Gly Glu Glu Pro Val Phe Val Val Thr Gly Arg Lys Glu
            20                  25                  30

Asp Val Asn Lys Ala Lys Arg Glu Ile Leu Ser Ala Ala Asp His Phe
        35                  40                  45

Ser
```

```
<210> SEQ ID NO 14
<211> LENGTH: 64
<212> TYPE: PRT
<213> ORGANISM: Homo sapiens

<400> SEQUENCE: 14

Arg Val Pro Tyr Arg Val Val Gly Leu Val Val Gly Pro Lys Gly Ala
 1               5                  10                  15

Thr Ile Lys Arg Ile Gln Gln Gln Thr His Thr Tyr Ile Val Thr Pro
                20                  25                  30

Ser Arg Asp Lys Glu Pro Val Phe Glu Val Thr Gly Met Pro Glu Asn
            35                  40                  45

Val Asp Arg Ala Arg Glu Glu Ile Glu Ala His Ile Ala Leu Arg Thr
        50                  55                  60

<210> SEQ ID NO 15
<211> LENGTH: 64
<212> TYPE: PRT
<213> ORGANISM: Homo sapiens

<400> SEQUENCE: 15

Arg Val Pro Tyr Arg Val Val Gly Leu Val Val Gly Pro Lys Gly Ala
 1               5                  10                  15

Thr Ile Lys Arg Ile Gln Gln Thr Asn Thr Tyr Ile Ile Thr Pro
                20                  25                  30

Ser Arg Asp Arg Asp Pro Val Phe Glu Ile Thr Gly Ala Pro Gly Asn
            35                  40                  45

Val Glu Arg Ala Arg Glu Glu Ile Glu Thr His Ile Ala Val Arg Thr
        50                  55                  60

<210> SEQ ID NO 16
<211> LENGTH: 64
<212> TYPE: PRT
<213> ORGANISM: Homo sapiens

<400> SEQUENCE: 16

Arg Val Pro Tyr Arg Val Val Gly Leu Val Val Gly Pro Lys Gly Ala
 1               5                  10                  15

Thr Ile Lys Arg Ile Gln Gln Gln Thr His Thr Tyr Ile Val Thr Pro
                20                  25                  30

Ser Arg Asp Lys Glu Pro Val Phe Glu Val Thr Gly Met Pro Glu Asn
            35                  40                  45

Val Asp Arg Ala Arg Glu Glu Ile Glu Met His Ile Ala Met Arg Thr
        50                  55                  60

<210> SEQ ID NO 17
<211> LENGTH: 64
<212> TYPE: PRT
<213> ORGANISM: Homo sapiens

<400> SEQUENCE: 17

Arg Val Pro Tyr Arg Val Val Gly Leu Val Val Gly Pro Lys Gly Ala
 1               5                  10                  15

Thr Ile Lys Arg Ile Gln Gln Arg Thr His Thr Tyr Ile Val Thr Pro
                20                  25                  30

Gly Arg Asp Lys Glu Pro Val Phe Ala Val Thr Gly Met Pro Glu Asn
            35                  40                  45

Val Asp Arg Ala Arg Glu Glu Ile Glu Ala His Ile Thr Leu Arg Thr
        50                  55                  60
```

```
<210> SEQ ID NO 18
<211> LENGTH: 64
<212> TYPE: PRT
<213> ORGANISM: Caenorhabditis elegans

<400> SEQUENCE: 18

Arg Val Pro Leu Arg Val Val Gly Leu Val Val Gly Pro Lys Gly Ala
1               5                   10                  15

Thr Ile Lys Arg Ile Gln Gln Asp Thr His Thr Tyr Ile Ile Thr Pro
            20                  25                  30

Ser Arg Glu Arg Glu Pro Val Phe Glu Val Thr Gly Leu Pro His Asn
        35                  40                  45

Val Glu Ala Ala Arg Lys Glu Ile Glu Thr His Ile Phe Gln Arg Thr
    50                  55                  60

<210> SEQ ID NO 19
<211> LENGTH: 64
<212> TYPE: PRT
<213> ORGANISM: Ciona savignyi

<400> SEQUENCE: 19

Arg Val Pro Tyr Arg Val Val Gly Leu Val Val Gly Pro Lys Gly Ala
1               5                   10                  15

Thr Ile Lys Arg Ile Gln Gln Gln Thr His Thr Tyr Ile Val Thr Pro
            20                  25                  30

Ser Arg Asp Lys Glu Pro Val Phe Glu Val Thr Gly Leu Pro Glu Asn
        35                  40                  45

Val Glu Lys Ala Lys Glu Glu Ile Glu Ala His Ile Ala Thr Arg Thr
    50                  55                  60

<210> SEQ ID NO 20
<211> LENGTH: 64
<212> TYPE: PRT
<213> ORGANISM: Drosophila melanogaster

<400> SEQUENCE: 20

Arg Val Pro Tyr Arg Val Val Gly Leu Val Val Gly Pro Lys Gly Ala
1               5                   10                  15

Thr Ile Lys His Ile Gln Gln Glu Thr Gln Thr Tyr Ile Val Thr Pro
            20                  25                  30

Ser Arg Glu Lys Glu Pro Ile Phe Glu Val Thr Gly Leu Pro Asp Asn
        35                  40                  45

Val Asp Thr Ala Arg Lys Gln Ile Glu Ala His Ile Ala Leu Arg Thr
    50                  55                  60

<210> SEQ ID NO 21
<211> LENGTH: 42
<212> TYPE: PRT
<213> ORGANISM: Homo sapiens

<400> SEQUENCE: 21

Asp Cys Ser Val Cys Phe Glu Ser Glu Val Ile Ala Ala Leu Val Pro
1               5                   10                  15

Cys Gly His Asn Leu Phe Cys Met Glu Cys Ala Asn Arg Ile Cys Glu
            20                  25                  30

Lys Ser Glu Pro Glu Cys Pro Val Cys His
        35                  40
```

<210> SEQ ID NO 22
<211> LENGTH: 42
<212> TYPE: PRT
<213> ORGANISM: Homo sapiens

<400> SEQUENCE: 22

Asp Cys Met Val Cys Phe Glu Ser Glu Val Thr Ala Ala Leu Val Pro
 1               5                  10                  15

Cys Gly His Asn Leu Phe Cys Met Glu Cys Ala Val Arg Ile Cys Glu
            20                  25                  30

Arg Thr Asp Pro Glu Cys Pro Val Cys His
        35                  40

<210> SEQ ID NO 23
<211> LENGTH: 42
<212> TYPE: PRT
<213> ORGANISM: Homo sapiens

<400> SEQUENCE: 23

Asp Cys Val Ile Cys Phe Glu Asn Glu Val Ile Ala Ala Leu Val Pro
 1               5                  10                  15

Cys Gly His Asn Leu Phe Cys Met Glu Cys Ala Asn Lys Ile Cys Glu
            20                  25                  30

Lys Arg Thr Pro Ser Cys Pro Val Cys Gln
        35                  40

<210> SEQ ID NO 24
<211> LENGTH: 42
<212> TYPE: PRT
<213> ORGANISM: Homo sapiens

<400> SEQUENCE: 24

Glu Cys Val Val Cys Ala Glu Gly Glu Val Met Ala Ala Leu Val Pro
 1               5                  10                  15

Cys Gly His Asn Leu Phe Cys Met Asp Cys Ala Val Arg Ile Cys Gly
            20                  25                  30

Lys Ser Glu Pro Glu Cys Pro Ala Cys Arg
        35                  40

<210> SEQ ID NO 25
<211> LENGTH: 42
<212> TYPE: PRT
<213> ORGANISM: Ciona savignyi

<400> SEQUENCE: 25

Arg Cys Thr Leu Cys Asn Asp Gly Ser Val Val Ala Thr Leu Met Pro
 1               5                  10                  15

Cys Arg His Gln Val Phe Cys Phe Pro Cys Ala Asn Arg Val Val Ser
            20                  25                  30

Arg Ser Ala Ser Phe Cys Pro Tyr Cys His
        35                  40

<210> SEQ ID NO 26
<211> LENGTH: 42
<212> TYPE: PRT
<213> ORGANISM: Drosophila melanogaster

<400> SEQUENCE: 26

Glu Cys Phe Val Cys Asn Glu Asn Thr Val Thr Thr Ala Leu Val Pro
 1               5                  10                  15

Cys Gly His Asn Met Phe Cys Met Glu Cys Ala Asn His Ile Cys Leu

```
                   20                  25                  30
    Ser Met Asp Ala Val Cys Pro Val Cys Asn
             35                  40

<210> SEQ ID NO 27
<211> LENGTH: 434
<212> TYPE: PRT
<213> ORGANISM: Homo sapiens

<400> SEQUENCE: 27

Met Ile Arg Ala Ser Arg Asn Lys Asn Thr Ala Leu Asn Gly Ala Val
  1               5                  10                  15

Pro Gly Pro Pro Asn Leu Pro Gly Gln Thr Thr Ile Gln Val Arg Val
                 20                  25                  30

Pro Tyr Arg Val Val Gly Leu Val Gly Pro Lys Gly Ala Thr Ile
             35                  40                  45

Lys Arg Ile Gln Gln Gln Thr His Thr Tyr Ile Val Thr Pro Ser Arg
 50                  55                  60

Asp Lys Glu Pro Val Phe Glu Val Thr Gly Met Pro Glu Asn Val Asp
 65                  70                  75                  80

Arg Ala Arg Glu Glu Ile Glu Ala His Ile Ala Leu Arg Thr Gly Gly
                 85                  90                  95

Ile Ile Glu Leu Thr Asp Glu Asn Asp Phe His Ala Asn Gly Thr Asp
                100                 105                 110

Val Gly Phe Asp Leu His His Gly Ser Gly Ser Gly Pro Gly Ser
            115                 120                 125

Leu Trp Ser Lys Pro Thr Pro Ser Ile Thr Pro Thr Pro Gly Arg Lys
130                 135                 140

Pro Phe Ser Ser Tyr Arg Asn Asp Ser Ser Ser Ser Leu Gly Ser Ala
145                 150                 155                 160

Ser Thr Asp Ser Tyr Phe Gly Gly Gly Thr Ser Ser Ala Ala Ala
                165                 170                 175

Thr Gln Arg Leu Ala Asp Tyr Ser Pro Pro Ser Pro Ala Leu Ser Phe
            180                 185                 190

Ala His Asn Gly Asn Asn Asn Asn Gly Asn Gly Tyr Thr Tyr Thr
            195                 200                 205

Ala Gly Gly Glu Ala Ser Val Pro Ser Pro Asp Gly Cys Pro Glu Leu
        210                 215                 220

Gln Pro Thr Phe Asp Pro Ala Pro Ala Pro Pro Gly Ala Pro Leu
225                 230                 235                 240

Ile Trp Ala Gln Phe Glu Arg Ser Pro Gly Gly Pro Ala Ala Pro
                245                 250                 255

Val Ser Ser Ser Cys Ser Ser Ser Ala Ser Ser Ser Ala Ser Ser Ser
            260                 265                 270

Ser Val Val Phe Pro Gly Gly Gly Ala Ser Ala Pro Ser Asn Ala Asn
            275                 280                 285

Leu Gly Leu Leu Val His Arg Arg Leu His Pro Gly Thr Ser Cys Pro
    290                 295                 300

Arg Leu Ser Pro Pro Leu His Met Ala Pro Ala Gly Glu His His
305                 310                 315                 320

Leu Ala Arg Arg Val Arg Ser Asp Pro Gly Gly Gly Leu Ala Tyr
                325                 330                 335

Ala Ala Tyr Ala Asn Gly Leu Gly Ala Gln Leu Pro Gly Leu Gln Pro
            340                 345                 350
```

Ser Asp Thr Ser Gly Ser Ser Ser Ser Ser Ser Ser Ser
        355                 360                 365

Ser Ser Ser Ser Gly Leu Arg Arg Lys Gly Ser Arg Asp Cys Ser
    370                 375                 380

Val Cys Phe Glu Ser Glu Val Ile Ala Ala Leu Val Pro Cys Gly His
385                 390                 395                 400

Asn Leu Phe Cys Met Glu Cys Ala Asn Arg Ile Cys Glu Lys Ser Glu
                405                 410                 415

Pro Glu Cys Pro Val Cys His Thr Ala Val Thr Gln Ala Ile Arg Ile
            420                 425                 430

Phe Ser

<210> SEQ ID NO 28
<211> LENGTH: 340
<212> TYPE: PRT
<213> ORGANISM: Homo sapiens

<400> SEQUENCE: 28

Gly Gly Ile Ile Glu Leu Thr Asp Glu Asn Asp Phe His Ala Asn Gly
1               5                   10                  15

Thr Asp Val Gly Phe Asp Leu His His Gly Ser Gly Ser Gly Pro
            20                  25                  30

Gly Ser Leu Trp Ser Lys Pro Thr Pro Ser Ile Thr Pro Thr Pro Gly
        35                  40                  45

Arg Lys Pro Phe Ser Ser Tyr Arg Asn Asp Ser Ser Ser Ser Leu Gly
    50                  55                  60

Ser Ala Ser Thr Asp Ser Tyr Phe Gly Gly Gly Thr Ser Ser Ser Ala
65                  70                  75                  80

Ala Ala Thr Gln Arg Leu Ala Asp Tyr Ser Pro Pro Ser Pro Ala Leu
                85                  90                  95

Ser Phe Ala His Asn Gly Asn Asn Asn Asn Gly Asn Gly Tyr Thr
            100                 105                 110

Tyr Thr Ala Gly Gly Glu Ala Ser Val Pro Ser Pro Asp Gly Cys Pro
        115                 120                 125

Glu Leu Gln Pro Thr Phe Asp Pro Ala Pro Ala Pro Pro Gly Ala
    130                 135                 140

Pro Leu Ile Trp Ala Gln Phe Glu Arg Ser Pro Gly Gly Gly Pro Ala
145                 150                 155                 160

Ala Pro Val Ser Ser Cys Ser Ser Ser Ala Ser Ser Ser Ala Ser
                165                 170                 175

Ser Ser Ser Val Val Phe Pro Gly Gly Gly Ala Ser Ala Pro Ser Asn
            180                 185                 190

Ala Asn Leu Gly Leu Leu Val His Arg Arg Leu His Pro Gly Thr Ser
        195                 200                 205

Cys Pro Arg Leu Ser Pro Pro Leu His Met Ala Pro Gly Ala Gly Glu
    210                 215                 220

His His Leu Ala Arg Arg Val Arg Ser Asp Pro Gly Gly Gly Leu
225                 230                 235                 240

Ala Tyr Ala Ala Tyr Ala Asn Gly Leu Gly Ala Gln Leu Pro Gly Leu
                245                 250                 255

Gln Pro Ser Asp Thr Ser Gly Ser Ser Ser Ser Ser Ser Ser Ser
            260                 265                 270

Ser Ser Ser Ser Ser Ser Gly Leu Arg Arg Lys Gly Ser Arg Asp
        275                 280                 285

```
Cys Ser Val Cys Phe Glu Ser Glu Val Ile Ala Ala Leu Val Pro Cys
        290                 295                 300
Gly His Asn Leu Phe Cys Met Glu Cys Ala Asn Arg Ile Cys Glu Lys
305                 310                 315                 320
Ser Glu Pro Glu Cys Pro Val Cys His Thr Ala Val Thr Gln Ala Ile
                325                 330                 335
Arg Ile Phe Ser
            340

<210> SEQ ID NO 29
<211> LENGTH: 162
<212> TYPE: PRT
<213> ORGANISM: Homo sapiens

<400> SEQUENCE: 29

Ser Val Val Phe Pro Gly Gly Ala Ser Ala Pro Ser Asn Ala Asn
  1               5                  10                  15
Leu Gly Leu Leu Val His Arg Arg Leu His Pro Gly Thr Ser Cys Pro
                20                  25                  30
Arg Leu Ser Pro Pro Leu His Met Ala Pro Gly Ala Gly Glu His His
            35                  40                  45
Leu Ala Arg Arg Val Arg Ser Asp Pro Gly Gly Gly Leu Ala Tyr
        50                  55                  60
Ala Ala Tyr Ala Asn Gly Leu Gly Ala Gln Leu Pro Gly Leu Gln Pro
65                  70                  75                  80
Ser Asp Thr Ser Gly Ser Ser Ser Ser Ser Ser Ser Ser Ser Ser
                85                  90                  95
Ser Ser Ser Ser Ser Gly Leu Arg Arg Lys Gly Ser Arg Asp Cys Ser
                100                 105                 110
Val Cys Phe Glu Ser Glu Val Ile Ala Ala Leu Val Pro Cys Gly His
            115                 120                 125
Asn Leu Phe Cys Met Glu Cys Ala Asn Arg Ile Cys Glu Lys Ser Glu
        130                 135                 140
Pro Glu Cys Pro Val Cys His Thr Ala Val Thr Gln Ala Ile Arg Ile
145                 150                 155                 160
Phe Ser

<210> SEQ ID NO 30
<211> LENGTH: 510
<212> TYPE: PRT
<213> ORGANISM: Homo sapiens

<400> SEQUENCE: 30

Met Pro Ser Ser Leu Phe Ala Asp Leu Glu Arg Asn Gly Ser Gly Gly
  1               5                  10                  15
Gly Gly Gly Gly Ser Ser Gly Gly Glu Thr Leu Asp Asp Gln Arg
                20                  25                  30
Ala Leu Gln Leu Ala Leu Asp Gln Leu Ser Leu Gly Leu Asp Ser
            35                  40                  45
Asp Glu Gly Ala Ser Leu Tyr Asp Ser Glu Pro Arg Lys Lys Ser Val
        50                  55                  60
Asn Met Thr Glu Cys Val Pro Val Pro Ser Ser Glu His Val Ala Glu
65                  70                  75                  80
Ile Val Gly Arg Gln Gly Cys Lys Ile Lys Ala Leu Arg Ala Lys Thr
                85                  90                  95
Asn Thr Tyr Ile Lys Thr Pro Val Arg Gly Glu Glu Pro Val Phe Val
```

-continued

```
            100                 105                 110
Val Thr Gly Arg Lys Glu Asp Val Ala Met Ala Arg Arg Glu Ile Ile
        115                 120                 125

Ser Ala Ala Glu His Phe Ser Met Ile Arg Ala Ser Arg Asn Lys Asn
    130                 135                 140

Thr Ala Leu Asn Gly Ala Val Pro Gly Pro Asn Leu Pro Gly Gln
145                 150                 155                 160

Thr Thr Ile Gln Val Arg Val Pro Tyr Arg Val Val Gly Leu Val Val
                165                 170                 175

Gly Pro Lys Gly Ala Thr Ile Lys Arg Ile Gln Gln Gln Thr His Thr
            180                 185                 190

Tyr Ile Val Thr Pro Ser Arg Asp Lys Glu Pro Val Phe Glu Val Thr
        195                 200                 205

Gly Met Pro Glu Asn Val Asp Arg Ala Arg Glu Glu Ile Glu Ala His
    210                 215                 220

Ile Ala Leu Arg Thr Gly Gly Ile Ile Glu Leu Thr Asp Glu Asn Asp
225                 230                 235                 240

Phe His Ala Asn Gly Thr Asp Val Gly Phe Asp Leu His His Gly Ser
                245                 250                 255

Gly Gly Ser Gly Pro Gly Ser Leu Trp Ser Lys Pro Thr Pro Ser Ile
            260                 265                 270

Thr Pro Thr Pro Gly Arg Lys Pro Phe Ser Ser Tyr Arg Asn Asp Ser
        275                 280                 285

Ser Ser Ser Leu Gly Ser Ala Ser Thr Asp Ser Tyr Phe Gly Gly Gly
    290                 295                 300

Thr Ser Ser Ser Ala Ala Ala Thr Gln Arg Leu Ala Asp Tyr Ser Pro
305                 310                 315                 320

Pro Ser Pro Ala Leu Ser Phe Ala His Asn Gly Asn Asn Asn Asn
                325                 330                 335

Gly Asn Gly Tyr Thr Tyr Thr Ala Gly Gly Glu Ala Ser Val Pro Ser
            340                 345                 350

Pro Asp Gly Cys Pro Glu Leu Gln Pro Thr Phe Asp Pro Ala Pro Ala
        355                 360                 365

Pro Pro Pro Gly Ala Pro Leu Ile Trp Ala Gln Phe Glu Arg Ser Pro
370                 375                 380

Gly Gly Gly Pro Ala Ala Pro Val Ser Ser Ser Cys Ser Ser Ser Ala
385                 390                 395                 400

Ser Ser Ser Ala Ser Ser Ser Val Val Phe Pro Gly Gly Gly Ala
                405                 410                 415

Ser Ala Pro Ser Asn Ala Asn Leu Gly Leu Leu Val His Arg Arg Leu
            420                 425                 430

His Pro Gly Thr Ser Cys Pro Arg Leu Ser Pro Pro Leu His Met Ala
        435                 440                 445

Pro Gly Ala Gly Glu His His Leu Ala Arg Arg Val Arg Ser Asp Pro
    450                 455                 460

Gly Gly Gly Gly Leu Ala Tyr Ala Ala Tyr Ala Asn Gly Leu Gly Ala
465                 470                 475                 480

Gln Leu Pro Gly Leu Gln Pro Ser Asp Thr Ser Gly Ser Ser Ser Ser
                485                 490                 495

Ser Ser Ser Ser Ser Ser Ser Ser Ser Ser Ser Gly Leu
            500                 505                 510

<210> SEQ ID NO 31
```

```
<211> LENGTH: 492
<212> TYPE: PRT
<213> ORGANISM: Homo sapiens

<400> SEQUENCE: 31

Met Pro Ser Ser Leu Phe Ala Asp Leu Glu Arg Asn Gly Ser Gly Gly
1               5                   10                  15

Gly Gly Gly Gly Ser Ser Gly Gly Glu Thr Leu Asp Asp Gln Arg
            20                  25                  30

Ala Leu Gln Leu Ala Leu Asp Gln Leu Ser Leu Leu Gly Leu Asp Ser
            35                  40                  45

Asp Glu Gly Ala Ser Leu Tyr Asp Ser Glu Pro Arg Lys Lys Ser Val
50                  55                  60

Asn Met Thr Glu Cys Val Pro Val Pro Ser Ser Glu His Val Ala Glu
65                  70                  75                  80

Ile Val Gly Arg Gln Gly Cys Lys Ile Lys Ala Leu Arg Ala Lys Thr
                85                  90                  95

Asn Thr Tyr Ile Lys Thr Pro Val Arg Gly Glu Pro Val Phe Val
            100                 105                 110

Val Thr Gly Arg Lys Glu Asp Val Ala Met Ala Arg Arg Glu Ile Ile
            115                 120                 125

Ser Ala Ala Glu His Phe Ser Met Ile Arg Ala Ser Arg Asn Lys Asn
130                 135                 140

Thr Ala Leu Asn Gly Ala Val Pro Gly Pro Pro Asn Leu Pro Gly Gln
145                 150                 155                 160

Thr Thr Ile Gln Val Arg Val Pro Tyr Arg Val Val Gly Leu Val Val
                165                 170                 175

Gly Pro Lys Gly Ala Thr Ile Lys Arg Ile Gln Gln Gln Thr His Thr
            180                 185                 190

Tyr Ile Val Thr Pro Ser Arg Asp Lys Glu Pro Val Phe Glu Val Thr
            195                 200                 205

Gly Met Pro Glu Asn Val Asp Arg Ala Arg Glu Glu Ile Glu Ala His
210                 215                 220

Ile Ala Leu Arg Thr Gly Gly Ile Ile Glu Leu Thr Asp Glu Asn Asp
225                 230                 235                 240

Phe His Ala Asn Gly Thr Asp Val Gly Phe Asp Leu His His Gly Ser
                245                 250                 255

Gly Gly Ser Gly Pro Gly Ser Leu Trp Ser Lys Pro Thr Pro Ser Ile
            260                 265                 270

Thr Pro Thr Pro Gly Arg Lys Pro Phe Ser Ser Tyr Arg Asn Asp Ser
            275                 280                 285

Ser Ser Ser Leu Gly Ser Ala Ser Thr Asp Ser Tyr Phe Gly Gly Gly
290                 295                 300

Thr Ser Ser Ser Ala Ala Ala Thr Gln Arg Leu Ala Asp Tyr Ser Pro
305                 310                 315                 320

Pro Ser Pro Ala Leu Ser Phe Ala His Asn Gly Asn Asn Asn Asn
                325                 330                 335

Gly Asn Gly Tyr Thr Tyr Thr Ala Gly Gly Glu Ala Ser Val Pro Ser
            340                 345                 350

Pro Asp Gly Cys Pro Glu Leu Gln Pro Thr Phe Asp Pro Ala Pro Ala
            355                 360                 365

Pro Pro Pro Gly Ala Pro Leu Ile Trp Ala Gln Phe Glu Arg Ser Pro
370                 375                 380

Gly Gly Gly Pro Ala Ala Pro Val Ser Ser Ser Cys Ser Ser Ser Ala
```

```
385                 390                 395                 400
Ser Ser Ser Ala Ser Ser Ser Val Val Phe Pro Gly Gly Ala
                405                 410                 415

Ser Ala Pro Ser Asn Ala Asn Leu Gly Leu Leu Val His Arg Arg Leu
            420                 425                 430

His Pro Gly Thr Ser Cys Pro Arg Leu Ser Pro Pro Leu His Met Ala
            435                 440                 445

Pro Gly Ala Gly Glu His His Leu Ala Arg Arg Val Arg Ser Asp Pro
            450                 455                 460

Gly Gly Gly Gly Leu Ala Tyr Ala Ala Tyr Ala Asn Gly Leu Gly Ala
465                 470                 475                 480

Gln Leu Pro Gly Leu Gln Pro Ser Asp Thr Ser Gly
            485                 490

<210> SEQ ID NO 32
<211> LENGTH: 392
<212> TYPE: PRT
<213> ORGANISM: Homo sapiens

<400> SEQUENCE: 32

Met Pro Ser Ser Leu Phe Ala Asp Leu Glu Arg Asn Gly Ser Gly Gly
 1               5                  10                  15

Gly Gly Gly Gly Ser Ser Gly Gly Glu Thr Leu Asp Asp Gln Arg
             20                  25                  30

Ala Leu Gln Leu Ala Leu Asp Gln Leu Ser Leu Leu Gly Leu Asp Ser
            35                  40                  45

Asp Glu Gly Ala Ser Leu Tyr Asp Ser Glu Pro Arg Lys Lys Ser Val
    50                  55                  60

Asn Met Thr Glu Cys Val Pro Val Pro Ser Ser Glu His Val Ala Glu
65                  70                  75                  80

Ile Val Gly Arg Gln Gly Cys Lys Ile Lys Ala Leu Arg Ala Lys Thr
                85                  90                  95

Asn Thr Tyr Ile Lys Thr Pro Val Arg Gly Glu Glu Pro Val Phe Val
            100                 105                 110

Val Thr Gly Arg Lys Glu Asp Val Ala Met Ala Arg Arg Glu Ile Ile
            115                 120                 125

Ser Ala Ala Glu His Phe Ser Met Ile Arg Ala Ser Arg Asn Lys Asn
130                 135                 140

Thr Ala Leu Asn Gly Ala Val Pro Gly Pro Pro Asn Leu Pro Gly Gln
145                 150                 155                 160

Thr Thr Ile Gln Val Arg Val Pro Tyr Arg Val Val Gly Leu Val Val
            165                 170                 175

Gly Pro Lys Gly Ala Thr Ile Lys Arg Ile Gln Gln Gln Thr His Thr
            180                 185                 190

Tyr Ile Val Thr Pro Ser Arg Asp Lys Glu Pro Val Phe Glu Val Thr
            195                 200                 205

Gly Met Pro Glu Asn Val Asp Arg Ala Arg Glu Glu Ile Glu Ala His
210                 215                 220
```

```
Ile Ala Leu Arg Thr Gly Gly Ile Ile Glu Leu Thr Asp Glu Asn Asp
225                 230                 235                 240

Phe His Ala Asn Gly Thr Asp Val Gly Phe Asp Leu His His Gly Ser
                245                 250                 255

Gly Gly Ser Gly Pro Gly Ser Leu Trp Ser Lys Pro Thr Pro Ser Ile
            260                 265                 270

Thr Pro Thr Pro Gly Arg Lys Pro Phe Ser Ser Tyr Arg Asn Asp Ser
        275                 280                 285

Ser Ser Ser Leu Gly Ser Ala Ser Thr Asp Ser Tyr Phe Gly Gly Gly
        290                 295                 300

Thr Ser Ser Ser Ala Ala Ala Thr Gln Arg Leu Ala Asp Tyr Ser Pro
305                 310                 315                 320

Pro Ser Pro Ala Leu Ser Phe Ala His Asn Gly Asn Asn Asn Asn Asn
                325                 330                 335

Gly Asn Gly Tyr Thr Tyr Thr Ala Gly Gly Glu Ala Ser Val Pro Ser
                340                 345                 350

Pro Asp Gly Cys Pro Glu Leu Gln Pro Thr Phe Asp Pro Ala Pro Ala
            355                 360                 365

Pro Pro Pro Gly Ala Pro Leu Ile Trp Ala Gln Phe Glu Arg Ser Pro
        370                 375                 380

Gly Gly Gly Pro Ala Ala Pro Val
385                 390

<210> SEQ ID NO 33
<211> LENGTH: 164
<212> TYPE: PRT
<213> ORGANISM: Homo sapiens

<400> SEQUENCE: 33

Met Pro Ser Ser Leu Phe Ala Asp Leu Glu Arg Asn Gly Ser Gly Gly
  1               5                  10                  15

Gly Gly Gly Gly Ser Ser Gly Gly Glu Thr Leu Asp Asp Gln Arg
                 20                  25                  30

Ala Leu Gln Leu Ala Leu Asp Gln Leu Ser Leu Gly Leu Asp Ser
             35                  40                  45

Asp Glu Gly Ala Ser Leu Tyr Asp Ser Glu Pro Arg Lys Lys Ser Val
     50                  55                  60

Asn Met Thr Glu Cys Val Pro Val Pro Ser Ser Glu His Val Ala Glu
 65                  70                  75                  80

Ile Val Gly Arg Gln Gly Cys Lys Ile Lys Ala Leu Arg Ala Lys Thr
                 85                  90                  95

Asn Thr Tyr Ile Lys Thr Pro Val Arg Gly Glu Glu Pro Val Phe Val
            100                 105                 110

Val Thr Gly Arg Lys Glu Asp Val Ala Met Ala Arg Arg Glu Ile Ile
        115                 120                 125

Ser Ala Ala Glu His Phe Ser Met Ile Arg Ala Ser Arg Asn Lys Asn
130                 135                 140

Thr Ala Leu Asn Gly Ala Val Pro Gly Pro Pro Asn Leu Pro Gly Gln
145                 150                 155                 160

Thr Thr Ile Gln
```

APOPTOSIS-INDUCING GENE AND UTILIZATION OF THE SAME

TECHNICAL FIELD

The present invention relates to an apoptosis-inducing gene, and more specifically to a gene that is expressed at a high level when apoptosis is induced by TGF-β. The present invention also relates to a method for screening an agent using the above apoptosis-inducing gene.

BACKGROUND ART

Apoptosis means a process in which a certain cell leads to death as a result of programmed cell death in the development, differentiation, and maturation of cells or individuals, or as a result of cell death that is induced under various circumstances. It is considered that such apoptosis takes place under various physiological conditions. The morphological characteristics of apoptosis include absence of contact with surrounding cells, concentration of the cytoplasm, condensation of the chromatin or nucleus associated with the activity of endonuclease, segmentation of the nucleus, and the like. Regarding such apoptosis, disappearance of microvillus on the cell surface, smoothing of the cell surface (formation of bubbles on the cell surface; membranece blebbing), and the like are also observed. It has been reported that a phenomenon is also observed where DNA is fragmentized by endonuclease activity, and the final cell fragment as an apoptotic body has a mechanism whereby it is englobed by cells adjacent thereto [Immunology Today, 7 (4), 115-119 (1986)].

It has been clarified that apoptosis has an important relationship with various types of diseases. In recent years, various attempts have been made to diagnose, prevent, and treat such diseases by inducing or suppressing the apoptosis of cells.

Apoptosis is also call programmed cell death, and this term means a certain type of cell death occurring as a normal physiological process in many tissues. Apoptosis takes place as a result of activation of a genetic program provided in a cell itself. Finally, such apoptotic cells are removed by surrounding phagocytes without causing any inflammation (Shigekazu Nagata, (1998), Jikken Igaku (Experimental Medicine), Vol. 16, 1242-1246). It has been known that apoptosis is associated with not only a normal physiological process, but also with the onset of serious diseases such as cancer, autoimmune disease, or neurodegenerative disease. Thus, it is strongly desired that a method for inducing or inhibiting apoptosis so as to treat the aforementioned diseases, and an agent useful for such a method, will be developed. With regard to an apoptosis-inducing mechanism, the following facts have been clarified in detail to date. That is, apoptosis takes place as a result of a process of inducing apoptosis by a Fas antigen or a ligand of a tumor necrosis factor receptor that binds to its receptor located on the surface of an animal cell (Nagata, S., (1997) Cell, 88, 355-365), or as a result of activation of an intracellular pathway that induces apoptosis, due to cancer cells damaged by anticancer agents or X-ray irradiation (Haldar, S., et al., (1995) Proc. Natl. Acad. Sci. USA 92, 4507-4511).

DISCLOSURE OF THE INVENTION

If a gene that is activated and specifically expressed during apoptosis induction in cells were provided, it would become possible to clarify such apoptosis or the pathologic conditions of apoptosis-related diseases and to establish a method for diagnosing and treating the diseases, by analyzing the gene expression level in each cell, the structure thereof, and the functions thereof, and also by analyzing the expression product.

It is a first object of the present invention to provide a protein useful for searching an apoptosis-inhibiting substance or an apoptosis-promoting substance, a gene encoding the above protein, a vector comprising the above gene, and a transformant comprising the above vector.

It is a second object of the present invention to provide a method for screening an apoptosis-inhibiting substance or an apoptosis-promoting substance that acts on the above-described protein as a target, and an apoptosis-inhibiting substance or an apoptosis-promoting substance.

The present inventors have intensively studied to achieve the aforementioned objects. Using a microarray, they have studied comprehensive isolation of a gene that is induced to be expressed by TGF-β. During such a process, the inventors have identified D8 as a gene, the expression level of which is significantly different depending on TGF-β. The full-length D8 was recovered by PCR using a human testis library as a template, and the nucleotide sequence thereof was determined. As a result, it was found that the full length of D8 consists of 1,710 bases, that is, 569 amino acids, and that it comprises two KH domains functioning as RNA-binding motifs on the N-terminal side, a Ring finger domain functioning as ubiquitin ligase E3 on the C-terminal side, and a serine-rich region in the center whose functions remain unknown. Moreover, the present inventors have demonstrated that apoptosis can be suppressed by the RNAi effects of D8. The present invention has been completed based on these findings.

That is to say, the present invention provides an apoptosis-inducing protein (hereinafter referred to as the protein of the present invention at times) of any one of the following (a), (b), and (c):

(a) a protein having the amino acid sequence shown in SEQ ID NO: 2 of the sequence listing;
(b) a protein, which has an amino acid sequence comprising a deletion, substitution, and/or addition of one or several amino acids with respect to the amino acid sequence shown in SEQ ID NO: 2 of the sequence listing, and has activity of inducing apoptosis; and
(c) a protein, which has an amino acid sequence showing homology of 95% or more with the amino acid sequence shown in SEQ ID NO: 2 of the sequence listing, and has activity of inducing apoptosis.

In another aspect, the present invention provides an apoptosis-inducing gene encoding the protein of the present invention (hereinafter referred to as the gene of the present invention at times). The gene of the present invention is preferably an apoptosis-inducing gene of any one of the following (a), (b), and (c):

(a) a gene having the nucleotide sequence shown in SEQ ID NO: 1 of the sequence listing;
(b) a gene, which has a nucleotide sequence comprising a deletion, substitution, and/or addition of one or several nucleotides with respect to the nucleotide sequence shown in SEQ ID NO: 1 of the sequence listing, and encodes the protein having activity of inducing apoptosis; and
(c) a gene, which has a nucleotide sequence hybridizing with the nucleotide sequence shown in SEQ ID NO: 1 of the sequence listing under stringent conditions, and encodes the protein having activity of inducing apoptosis.

In another aspect, the present invention provides a recombinant vector comprising the gene of the present invention.

In another aspect, the present invention provides a transformant comprising the above-described recombinant vector.

In another aspect, the present invention provides a method for producing the protein of the present invention, which comprises culturing the above-described transformant and collecting the protein of the present invention from the obtained culture.

In another aspect, the present invention provides an antibody against the apoptosis-inducing protein of the present invention.

In another aspect, the present invention provides an apoptosis-inhibiting agent comprising the above-described antibody.

In another aspect, the present invention provides an oligonucleotide comprising at least 10 contiguous nucleotides in the nucleotide sequence of the apoptosis-inducing gene of the present invention, and an antisense oligonucleotide having a sequence that is complementary to that of the above oligonucleotide.

In another aspect, the present invention provides an apoptosis-inhibiting agent, which comprises an antisense oligonucleotide having a sequence that is complementary to that of the oligonucleotide comprising at least 10 contiguous nucleotides in the nucleotide sequence of the apoptosis-inducing gene of the present invention.

In another aspect, the present invention provides double-stranded RNA comprising at least 10 contiguous nucleotides in the nucleotide sequence of RNA transcribed from the nucleotide sequence of the apoptosis-inducing gene of the present invention, or DNA encoding the double-stranded RNA.

In another aspect, the present invention provides an apoptosis-inhibiting agent, which comprises the double-stranded RNA or DNA of the present invention.

In another aspect, the present invention provides a method for inhibiting apoptosis, which comprises inhibiting the expression of the apoptosis-inducing protein of the present invention and/or the functions thereof.

In another aspect, the present invention provides an apoptosis-inhibiting agent, which comprises a substance that inhibits the expression of the apoptosis-inducing protein of the present invention and/or the functions thereof.

In another aspect, the present invention provides a method for promoting apoptosis, which comprises increasing the expression of the apoptosis-inducing protein of the present invention and/or the functions thereof.

In another aspect, the present invention provides an apoptosis-promoting agent, which comprises a substance that increases the expression of the apoptosis-inducing protein of the present invention and/or the functions thereof.

In another aspect, the present invention provides a method for screening a substance that inhibits or promotes apoptosis, using a change in the expression of the apoptosis-inducing protein of the present invention and/or in the functions thereof as an indicator.

Preferably, there is provided a method for screening a substance that inhibits or promotes apoptosis, which comprises culturing cells having a gene encoding the apoptosis-inducing protein of the present invention, together with TGF-$\beta$, in the presence or absence of a test substance, and screening the above substance using, as an indicator, a change in the expression of the apoptosis-inducing protein of the present invention and/or in the functions thereof, which depends on the presence or absence of the test substance.

BRIEF DESCRIPTION OF THE DRAWINGS

FIG. 3 shows the alignments of two KH domains and a Ring finger domain of the D8 family (SEQ ID NOS 7-26, disclosed respectively in order of appearance).

FIG. 5 shows the results of the analysis of activation of a D8 promoter by TGF-$\beta$1.

FIG. 6 shows the results of the measurement of the effects of D8 on cell proliferation by colony formation assay.

BEST MODE FOR CARRYING OUT THE INVENTION

Figure 1:
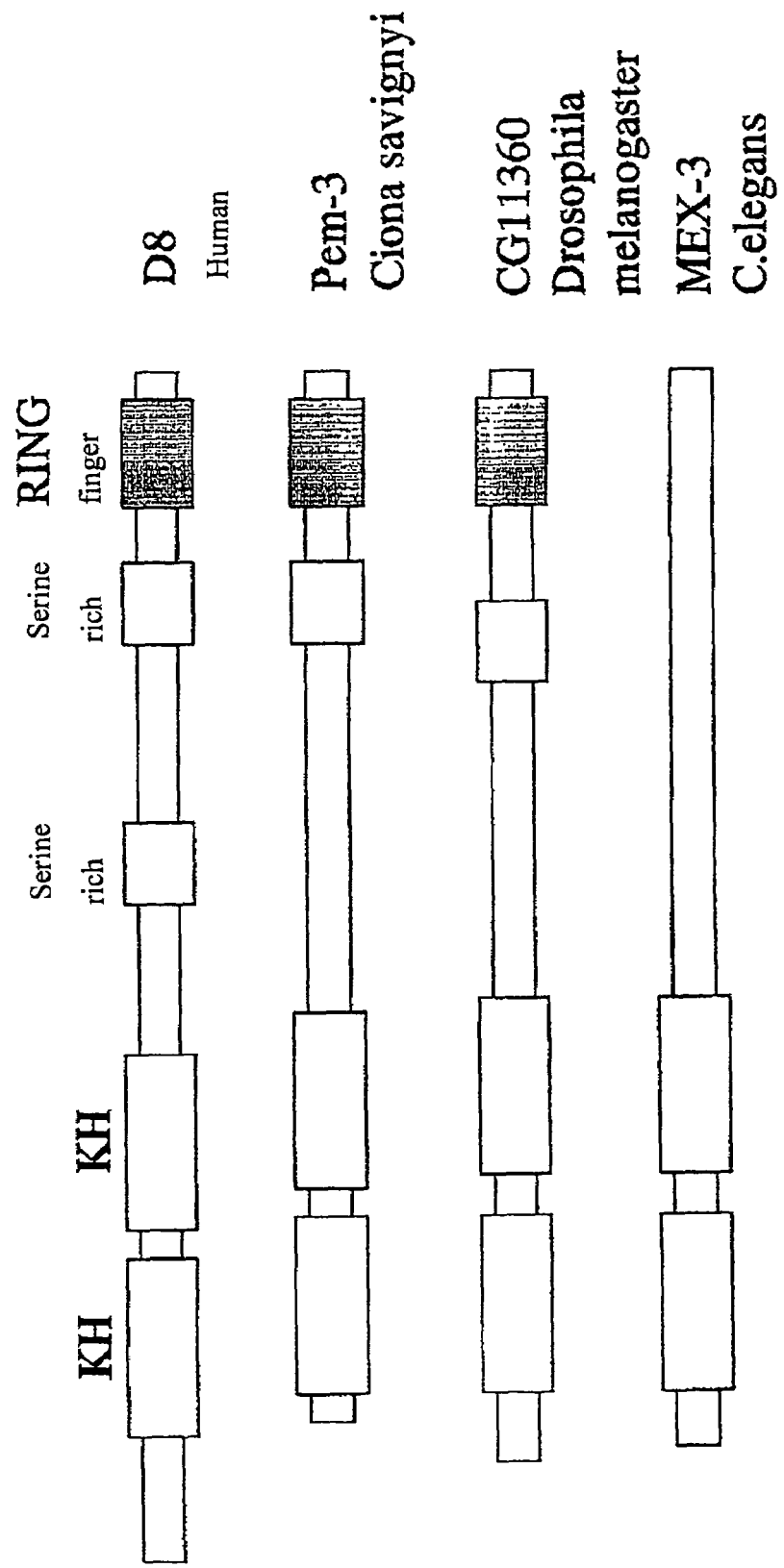
FIG. 1 shows a structure of the D8 family (human, nematode, and drosophila).

The embodiments of the present invention will be described in detail below.

(1) Apoptosis-Inducing Protein

The apoptosis-inducing protein of the present invention is any one of the following proteins:

(a) a protein having the amino acid sequence shown in SEQ ID NO: 2 of the sequence listing;

(b) a protein, which has an amino acid sequence comprising a deletion, substitution, and/or addition of one or several amino acids with respect to the amino acid sequence shown in SEQ ID NO: 2 of the sequence listing, and has activity of inducing apoptosis; and (c) a protein, which has an amino acid sequence showing homology of 95% or more with the amino acid sequence shown in SEQ ID NO: 2 of the sequence listing, and has activity of inducing apoptosis.

The range of the term "one or several" in the passage "an amino acid sequence comprising a deletion, substitution, and/or addition of one or several amino acids with respect to the amino acid sequence" is not particularly limited in the present specification. It is, for example, between 1 and 20, preferably between 1 and 10, more preferably between 1 and 7, further preferably between 1 and 5, and particularly preferably between 1 and 3.

The term "an amino acid sequence showing homology of 95% or more" is used in the present specification to mean that a homology of amino acids is at least 95%, preferably 96% or more, and more preferably 97% or more.

As stated above, proteins encoded by mutant genes showing high homology with the gene having the nucleotide sequence shown in SEQ ID NO: 1 of the sequence listing, which are physiologically active proteins having activity of inducing apoptosis, are all included in the scope of the present invention.

Amino acid side chains that become constitutional elements of a protein are different with respect to hydrophobicity, electric charge, size, and so on. Several highly conservative relationships, which do not substantially affect the three dimensional structure (which is also referred to as steric structure) of a protein as a whole, have been known from empirical facts or physicochemical measurements. Examples of substitution of amino acid residues may include: glycine (Gly) and proline (Pro); Gly and alanine (Ala) or valine (Val); leucine (Leu) and isoleucine (Ile); glutamic acid (Glu) and glutamine (Gln); aspartic acid (Asp) and asparagine (Asn); cysteine (Cys) and threonine (Thr); Thr and serine (Ser) or Ala; and lysine (Lys) and arginine (Arg).

Accordingly, mutant proteins comprising a substitution, insertion, deletion, or the like of amino acids on the amino acid sequence of D8 shown in SEQ ID NO: 2 of the sequence listing are all included in the scope of the present invention, as long as such mutant proteins are physiologically active proteins having activity of inducing apoptosis as with D8, and the mutation thereof is highly conservative in the three dimensional structure of D8.

The term "a protein having activity of inducing apoptosis" is used in the present specification to mean a protein having activity of promoting apoptosis induction by TGF-β. In general, such a protein has two KH domains as RNA-binding domains.

Whether or not a certain protein has activity of promoting apoptosis induction by TGF-β can be detected, for example, by introducing DNA encoding the above protein into cells where apoptosis can be induced by TGF-β, so as to allow it to transiently excessively express, and then examining whether or not such excessive expression of the DNA can increase the number of the cells where apoptosis is induced, when the apoptosis of the above cells is induced by addition of TGF-β.

A method for obtaining the protein of the present invention is not particularly limited. It may be a protein synthesized by chemical synthesis, a natural protein isolated from biological samples or cultured cells, or a recombinant protein produced by genetic recombination.

When a recombinant protein is produced, first, it is necessary to obtain a gene encoding the protein. A method for producing a recombinant protein using a recombinant gene and a suitable expression system will be described later in the present specification.

(2) Apoptosis-Inducing Gene

Genes encoding the proteins described in (1) above are all included in the scope of the present invention. Specific examples of the gene of the present invention include the gene of any one of the following (a), (b), and (c):

(a) a gene having the nucleotide sequence shown in SEQ ID NO: 1 of the sequence listing;
(b) a gene, which has a nucleotide sequence comprising a deletion, substitution, and/or addition of one or several nucleotides with respect to the nucleotide sequence shown in SEQ ID NO: 1 of the sequence listing, and encodes the protein having activity of inducing apoptosis; and
(c) a gene, which has a nucleotide sequence hybridizing with the nucleotide sequence shown in SEQ ID NO: 1 of the sequence listing under stringent conditions, and encodes the protein having activity of inducing apoptosis.

The range of the term "one or several" in the passage "a nucleotide sequence comprising a deletion, substitution, and/or addition of one or several nucleotides with respect to the nucleotide sequence" is not particularly limited in the present specification. It is, for example, between 1 and 60, preferably between 1 and 30, more preferably between 1 and 20, further preferably between 1 and 10, and particularly preferably between 1 and 5.

An example of the degree of the aforementioned DNA mutation may include a nucleotide sequence showing homology of 80% or more with the nucleotide sequence of the D8 gene shown in SEQ ID NO: 2 of the sequence listing.

The term "hybridizing with . . . under stringent conditions" is used in the present specification to mean hybridization with the D8 gene by Southern hybridization under ordinary conditions (for example, in a case where a probe is labeled with a DIG DNA Labeling kit (Cat No. 1175033 manufactured by Boehringer Mannheim), hybridization is carried out at 32° C. in a DIG Easy Hyb solution (Cat No. 1603558 manufactured by Boehringer Mannheim), and the membrane is then washed at 50° C. with 0.5×SSC solution (containing 0.1% [w/v] SDS) (wherein 1×SSC consists of 0.15 M NaCl and 0.015 M sodium citrate)). Such hybridization can be carried out according to the method described in Molecular Cloning, A laboratory Manual, 2nd Ed., Cold Spring Harbor Laboratory, Cold Spring Harbor, N.Y., 1989 (hereinafter abbreviated as Molecular Cloning 2nd Ed.); Current Protocols in Molecular Biology, Supplements 1-38, John Wiley & Sons (1987-1997) (hereinafter abbreviated as Current Protocols in Molecular Biology); and the like.

DNA hybridizing with another DNA under stringent conditions may be DNA having a certain level of homology with the nucleotide sequence of DNA used as a probe. For example, DNA showing homology of 80% or more, preferably 85% or more, more preferably 90% or more, further preferably 93% or more, particularly preferably 95% or more, and most preferably 98% or more, with the nucleotide sequence of DNA used as a probe, is used.

(3) Obtainment of the Gene of the Present Invention

A method for obtaining the gene of the present invention is not particularly limited. Appropriate probes or primers are prepared based on information regarding the nucleotide sequence and the amino acid sequence shown in SEQ ID NOS: 1 and 2, respectively, of the sequence listing of the present specification. Using them, desired clones are selected from a human cDNA library (which has been prepared according to a common method from appropriate cells in which the gene of the present invention is expressed), so as to isolate the gene of the present invention.

The gene of the present invention can also be obtained by the PCR method. For example, using chromosomal DNA or cDNA library derived from cultured human cells as a template, PCR is carried out with a set of primers that are designed to be able to amplify the nucleotide sequence shown in SEQ ID NO: 1.

PCR reaction conditions can appropriately be determined. For example, a cycle of reaction process consisting: of 94° C., 30 seconds (denaturation); 55° C., 30 seconds to 1 minute (annealing); and 72° C., 2 minutes (elongation) is repeated 30 times, and a reaction is then carried out at 72° C. for 7 minutes. Subsequently, the amplified DNA fragment can be cloned into a suitable vector that is capable of amplifying in a host such as *Escherichia coli*.

The aforementioned operations, such as preparation of probes or primers, construction of a cDNA library, screening of a cDNA library, or cloning of a gene of interest, are already known to persons skilled in the art. These operations can be carried out according to the methods described in Molecular Cloning $2^{nd}$ Ed., Current Protocols in Molecular Biology, etc.

In the present specification, the aforementioned gene (mutant gene), which has a nucleotide sequence comprising a deletion, substitution, and/or addition of one or several nucleotides with respect to the nucleotide sequence shown in SEQ ID NO: 1 of the sequence listing, and encodes a protein having activity of inducing apoptosis, can also be produced by any given methods that have already been known to persons skilled in the art, such as chemical synthesis, genetic engineering means, or mutagenesis. For example, mutant DNA can be obtained by using DNA having the nucleotide sequence shown in SEQ ID NO: 1 and introducing mutation into the above DNA. Specifically, mutant DNA can be obtained by a method of allowing such DNA having the nucleotide sequence shown in SEQ ID NO: 1 to come into contact with an agent used as a mutagene, a method of applying ultraviolet ray to the DNA, a genetic engineering method, or the like. Site-directed mutagenesis, which is one of the genetic engineering methods, is a useful method that is capable of introducing a specific mutation into a specific site. This method can be carried out according to the method described in Molecular Cloning $2^{nd}$ Ed., Current Protocols in Molecular Biology, or the like.

As stated above, DNA mutants having nucleotide sequences which are partially altered by various artificial treatments such as site-directed mutagenesis, random mutation by a treatment with a mutagenic agent, or a mutation, deletion ligation or the like of DNA fragments by cleavage with restriction enzymes, in connection with the nucleotide sequence of D8 gene of SEQ ID NO: 1 of the sequence listing, are also included in the scope of the present invention, as long as such DNA mutants encode proteins having activity of inducing apoptosis, although their sequences are different from the DNA sequence shown in SEQ ID NO: 2.

In the present specification, the aforementioned gene which has a nucleotide sequence hybridizing with the nucleotide sequence shown in SEQ ID NO: 1 of the sequence listing under stringent conditions, and encodes a protein having activity of inducing apoptosis, can be obtained by the colony hybridization method, the plaque hybridization method or the Southern blot hybridization method under the aforementioned certain hybridization conditions.

(4) Recombinant Vector

The recombinant vector of the present invention can be prepared by a common gene recombination technique that is carried out in a suitable host-vector system using the gene of the present invention. That is, the gene of the present invention can be inserted into a suitable vector, for its use. The type of a vector used in the present invention is not particularly limited. For example, the vector may be either an autonomously replicating vector (for example, a plasmid, etc.), or a vector that is incorporated into the genome of a host cell when it is introduced into the host cell and is then replicated together with the chromosome.

In addition, an expression vector can also be used as such a recombinant vector. Elements necessary for transcription (for example, a promoter, etc.) are functionally linked to the gene of the present invention that has been incorporated into an expression vector. A promoter is a DNA sequence exhibiting transcriptional activity in host cells, and it can appropriately be selected depending on the type of a host.

Examples of an appropriate vector used herein may include: *Escherichia coli*-derived plasmids (for example, pBR322, pUC118, etc.); *Bacillus subtilis*-derived plasmids (for example, pUB110, pSH19, etc.); and animal viruses such as bacteriophage, retrovirus, or vaccinia virus. For recombination, a translation initiation codon or a translation termination codon can be added using a suitable synthetic DNA adaptor.

A promoter used in an expression vector may appropriately be selected depending on the type of a host. For example, when *Escherichia coli* is used as a host, a T7 promoter, a lac promoter, a trp promoter, a XPL promoter, and the like can be used. When *Bacillus subtilis* is used as a host, an SOP promoter can be used. When yeast is used as a host, a PHO5 promoter, a GAP promoter, an ADH promoter, and the like can be used. When an animal cell is used as a host, an SV40-derived promoter, a retrovirus promoter, an MT-1 (metallothionein gene) promoter, and the like can be used. When an insect cell is used as a host, a polyhedrin promoter, a P10 promoter, an *Autographa californica* polyhedrosis basic protein promoter, a baculovirus immediate early gene 1 promoter, a baculovirus 39K delayed-early gene promoter, and the like can be used.

In addition, a human growth hormone terminator or the like may be functionally ligated to the gene of the present invention, as necessary. Moreover, in the case of using a fungal host, an appropriate terminator such as a TP11 terminator or an ADH3 terminator may be functionally ligated to the gene of the present invention. The recombinant vector of the present invention may further comprise elements such as a polyadenylation signal (for example, those derived from SV40 or an adenovirus 5E1b region), a transcription enhancer sequence (for example, an SV40 enhancer), or a translation enhancer sequence (for example, those encoding adenovirus VA RNA).

Moreover, the recombinant vector of the present invention may further comprise a DNA sequence enabling the replication of the above vector in host cells. An example of such a DNA sequence may be an SV40 replication origin (when host cells are mammalian cells).

Furthermore, the recombinant vector of the present invention may further comprise a selective marker. Examples of such a selective marker may include: genes whose complements are absent in host cells, such as a dihydrofolate reductase (DHFR) gene or a *Schizosaccharomyces pombe* TPI gene; and drug resistant genes such as ampicillin, kanamycin, tetracycline, chloramphenicol, neomycin or hygromycin resistant gene.

A method for ligating the gene of the present invention, a promoter, and as desired, a terminator and/or a secretory signal sequence to one another, and inserting the ligated product into a suitable vector, is well known to persons skilled in the art.

Moreover, it is also possible to allow the gene of the present invention to express in the form of a fusion protein with another protein (for example, glutathione S-transferase, protein A, or the like). The thus expressed fusion-type protein of the present invention can be cut out with suitable protease.

(5) Transformant of the Present Invention

A transformant can be produced by introducing the gene or recombinant vector of the present invention into a suitable host.

Any types of cells may be used as host cells into which the gene or recombinant vector of the present invention is introduced, as long as the DNA construction of the present invention can be allowed to express therein. Examples of such cells may include bacterial cells, yeast cells, fungal cells, and higher eukaryotic cells.

Examples of bacterial cells may include: Gram-positive bacteria such as bacteria belonging to genus *Bacillus* (for example, *Bacillus subtilis*) or bacteria belonging to genus *Streptomyces*; and Gram-negative bacteria such as *Escherichia coli*. Transformation of these bacteria may be carried out by the protoplast method or other known methods using competent cells.

Examples of mammalian cells may include HEK293 cells, HeLa cells, COS cells (for example, COS-7 cells, etc.), BHK cells, CHL cells, and CHO cells. A method of transforming mammalian cells to allow a gene introduced in the cells to express is also known. Examples of such a method used herein may include electroporation, the calcium phosphate method, and the lipofection method.

Examples of yeast cells may include cells belonging to genus *Saccharomyces* or genus *Schizosaccharomyces*. Specific examples may include *Saccharomyces cerevislae* and

*Saccharomyces kluyveri*. Examples of a method of introducing a recombinant vector into a yeast host may include electroporation, the spheroplast method, and the lithium acetate method.

Examples of other fugal cells may include cells belonging to filamentous fungi such as Aspergillus, Neurospora, Fusarium, or Trichoderma. When filamentous fungi are used as host cells, transformation can be carried out by incorporating a DNA construction into the chromosome of a host, so as to obtain recombinant host cells. Such incorporation of a DNA construction into a host chromosome can be carried out by homologous recombination, heterologous recombination, or the like, in accordance with known methods.

When insect cells are used as host cells, a recombinant gene-introduced vector and a baculovirus are co-introduced into insect cells, so as to obtain a recombinant virus in a supernatant of cultured insect cells. Thereafter, insect cells are infected with such a recombinant virus, so as to allow a protein to express therein (which is described, for example, in Baculovirus Expression Vectors, A Laboratory Manual; and Current Protocols in Molecular Biology, Bio/Technology, 6, 47 (1988)).

For example, an *Autographa californica* nuclear polyhedrosis virus, with which insects belonging to *Mamestra brassicae* are infected, can be used as a baculovirus.

Examples of insect cells may include: Sf9 and Sf21, ovarian cells of *Spodoptera frugiperda* [Baculovirus Expression Vectors, A Laboratory Manual, W. H. Freeman and Company, New York, (1992)]; and HiFive (manufactured by Invitrogen), ovarian cells of *Trichoplusia ni*.

Examples of a method of co-introducing a recombinant gene-introduced vector and the aforementioned baculovirus into insect cells, so as to prepare a recombinant virus, may include the calcium phosphate method and the lipofection method.

(6) Production of the Protein of the Present Invention Using Transformant

The aforementioned transformant is cultured in an appropriate nutrient medium under conditions that enable the expression of the introduced gene. In order to isolate and purify the protein of the present invention from the culture of the transformant, common methods for isolation and purification of proteins may be used.

When the protein of the present invention has been allowed to express in a dissolved state in cells, for example, after completion of the culture, the cells are recovered by centrifugation and are then suspended in an aqueous buffer solution. Thereafter, the cells are disintegrated with an ultrasonic disintegrator or the like, so as to obtain a cell-free extract. Common methods for isolation and purification of proteins, such as the solvent extraction method, the salting-out method using ammonium sulfate or the like, the desalination method, the precipitation method using organic solvents, anion exchange chromatography using resins such as diethylaminoethyl (DEAE) sepharose, cation exchange chromatography using resins such as S-Sepharose FF (manufactured by Pharmacia), hydrophobic chromatography using resins such as butyl sepharose or phenyl sepharose, the gel filtration method using a molecular sieve, affinity chromatography, chromatofocusing, electrophoresis such as the isoelectric focusing method, are performed, singly or in combination, on a supernatant obtained by centrifugation of the above cell-free extract, so as to obtain a purified sample.

(7) Antibody Against the Apoptosis-Inducing Protein

An antibody against the apoptosis-inducing protein of the present invention and an apoptosis-inhibiting agent using the same are also included in the scope of the present invention. Either a polyclonal antibody or a monoclonal antibody may be used as the antibody of the present invention, as long as it can specifically bind to the aforementioned apoptosis-inducing protein.

A polyclonal antibody can be prepared by separating and purifying the serum obtained from an animal that is immunized with an antigen. A monoclonal antibody can be prepared by producing hybridomas by fusing antibody-generating cells obtained from the animal immunized with an antigen, with myeloma cells; culturing the hybridomas, or administering them to an animal so as to cancerate the ascites thereof; and separating and purifying the obtained culture solution or ascites.

An antigen can be prepared by purifying the protein of the present invention from various types of cultured human cells. It can also be prepared by introducing a recombinant vector comprising DNA encoding a protein having the amino acid sequence shown in SEQ ID NO: 2, a mutant sequence thereof, or a portion thereof, into host cells such as *Escherichia coli*, yeast, animal cells, or insect cells, so as to allow the DNA to express therein, and then separating and purifying a protein obtained by expression of the above DNA. Further, an antigen can also be prepared by synthesizing a peptide having a partial sequence of the amino acid sequence shown in SEQ ID NO: 2, using an amino acid synthesizer.

As an immunization method, an antigen may directly be administered to non-human mammals such as a rabbit, a goat, a rat, a mouse, or a hamster, via a subcutaneous, intravenous, or intraperitoneal route. It is also preferable that an antigen be bound to carrier proteins with high antigenicity, such as Fissurellidae hemocyanin, keyhole limpet hemocyanin, bovine serum albumin, or bovine thyroglobulin, and the obtained mixture be then administered, or that an antigen be administered together with a suitable adjuvant such as Freund's complete adjuvant, aluminum hydroxide gel, or pertussis vaccine.

Such an antigen can be administered 3 to 10 times, every 1 or 2 weeks, after a first administration. Three to seven days after each administration, the blood is collected from the fundus oculi venous plexus. Whether or not the above serum reacts with the antigen used for immunization is examined by measuring an antibody titer according to enzyme immunoassay or the like. A non-human mammal, the serum of which exhibits a sufficient antibody titer to the antigen used for immunization, can be used as a source for supplying serum or antibody-generating cells. A polyclonal antibody can be prepared by separating and purifying the aforementioned serum.

A monoclonal antibody can be prepared by producing hybridomas by fusing the above antibody-generating cells with myeloma cells derived from non-human mammal; culturing the hybridomas, or administering the hybridomas to an animal so as to cancerate the ascites thereof; and separating and purifying the obtained culture solution or ascites. Examples of antibody-generating cells used herein may include antibody-generating cells contained in splenic cells, the lymph node, or the peripheral blood. Of these, splenic cells are particularly preferably used.

Examples of myeloma cells may include established cell lines derived from mice, such as the P3-X63Ag8-U1 (P3-U1) strain [Current Topics in Microbiology and Immunology, 18, 1-7 (1978)] that is a myeloma cell strain derived from 8-azaguanine resistant mouse (BALB/c); the P3-NS1/1-Ag4l (NS-1) strain [European J. Immunology, 6, 511-519 (1976)]; the SP2/0-Ag14 (SP-2) strain [Nature, 276, 269-270 (1978)]; the P3-X63-Ag8653 (653) strain [J. Immunology, 123, 1548-1550 (1979)]; or the P3-X63-Ag8 (X63) strain [Nature, 256, 495-497 (1975)].

Hybridomas can be produced by the following method. First, antibody-generating cells are mixed with myeloma cells, and the obtained mixture is suspended in an HAT medium [a medium obtained by adding hypoxanthine, thymidine, and aminopterin to a normal medium], followed by culture for 7 to 14 days. After completion of the culture, a portion of the culture supernatant is subjected to enzyme immunoassay or the like, so as to select cells which react with antigens but do not react with proteins containing no antigens. Subsequently, cloning is carried out by the limiting dilution method, so as to select cells that stably have a high antibody titer according to enzyme immunoassay, as monoclonal antibody-generating hybridomas. Thereafter, a monoclonal antibody can be prepared by separating and purifying it from the culture solution obtained by culturing the hybridomas, or from the cancerated ascites of an animal, to which the hybridomas have been intraperitoneally administered.

A method using, singly or in combination, centrifugation, ammonium sulfate precipitation, caprylic acid precipitation, or chromatography using a DEAE-sepharose column, an anion exchange column, a protein A or G column or a gel filtration column, is applied as a method of separating and purifying a polyclonal or monoclonal antibody.

The term "antibody" is used in the present specification to include not only full-length antibodies, but also antibody fragments. Such antibody fragments are preferably functional fragments such as F(ab')$_2$ or Fab'. Such F(ab')$_2$ and Fab' are produced by treating immunoglobulin with protease (for example, pepsin, papain, etc.). These are antibody fragments generated as a result of digestion before and after a disulfide bond existing between two H chains in a hinge region.

When the antibody of the present invention is used for administration to humans, in order to decrease immunogenicity, it is preferably used in the form of a human type antibody or humanized antibody. Such a human type antibody and a humanized antibody can be produced using mammals such as transgenic mice. Such a human type antibody is described in Morrison S. L. et al., Proc. Natl. Acad. Sci. USA, 81: 6851-6855 (1984), and Hiroshi Noguchi, *Igaku no Ayumi* (Progress of Medicine), 167: 457-462 (1993), for example. A humanized chemic antibody can be produced by binding a mouse antibody V region with a human antibody C region according to genetic recombination. A humanized antibody can be produced by substituting regions other than a complementarity-determining region (CDR) in a mouse monoclonal antibody, with sequences derived from a human antibody.

In addition, the antibody of the present invention can be used as an immobilized antibody that is immobilized on an insoluble carrier such as a solid-phase carrier, or as a labeled antibody that is labeled with a labeling substance. Such an immobilized antibody and a labeled antibody are also included in the scope of the present invention.

The aforementioned antibody of the present invention can be used to detect the protein of the present invention, or separate and purify it, utilizing its specificity. Moreover, among the antibodies of the present invention, those specifically binding to the apoptosis-inducing protein of the present invention, so as to inhibit its functions, can be used as apoptosis-inhibiting agents.

When the antibody of the present invention is used as an apoptosis-inhibiting agent in the form of a pharmaceutical composition, such a pharmaceutical composition can be prepared using the above antibody as an active ingredient and also using a pharmacologically acceptable carrier, a diluent (for example, an immunogenic adjuvant, etc.), a stabilizer, or an excipient. An apoptosis-inhibiting agent comprising the antibody of the present invention can be formulated by filtration sterilization and freeze-drying in the form of a prescription vial or a stabilized aqueous preparation.

Administration of such an apoptosis-inhibiting agent to patients can be carried out by methods known to persons skilled in the art, such as intraarterial injection, intravenous injection, or subcutaneous injection. The dosage is varied depending on the body weight or age of a patient, or an administration method. Persons skilled in the art can appropriately select a suitable dosage. The dosage of an antibody acting as an active ingredient is generally approximately between 0.1 μg and 100 mg per kg of body weight per once. The antibody of the present invention suppresses apoptosis, thereby exhibiting therapeutic effects on diseases associated with apoptosis promotion.

(8) Oligonucleotide and Antisense Oligonucleotide

On the basis of information regarding the nucleotide sequence of the D8 gene that has been clarified by the present invention, that is, using a probe or primer having a part of or the entire nucleotide sequence of the above gene, for example, the expression of the D8 gene can be detected in various types of human tissues. The expression of the D8 gene can be detected by a common method such as Northern blotting or RT-PCR. The D8 gene of the present invention is associated with induction of apoptosis in cells. As described later, since apoptosis is associated with various diseases, such apoptosis-associated diseases can be diagnosed by detecting the expression of the D8 gene.

When PCR is carried out, the type of a primer used is not particularly limited, as long as it can specifically amplify only the D8 gene of the present invention. Such primers can appropriately be designed based on the sequence information shown in SEQ ID NOS: 1 and 2. For example, an oligonucleotide comprising at least 10 contiguous nucleotides in the nucleotide sequence of the D8 gene, and an antisense oligonucleotide having a sequence complementary to the above oligonucleotide, can be used as a probe or a primer. More specifically, an oligonucleotide having a nucleotide sequence consisting of 10 to 60 contiguous residues, more preferably 10 to 40 contiguous residue, in the nucleotide sequence shown in SEQ ID NO: 1, and an antisense oligonucleotide having a sequence complementary to the above oligonucleotide, can be used.

The aforementioned oligonucleotide and antisense oligonucleotide can be produced by a common method using a DNA synthesizer. Examples of such an oligonucleotide and antisense oligonucleotide may include a sense primer corresponding to a nucleotide sequence portion on the 5'-terminal side of a partial nucleotide sequence of mRNA to be detected, and an antisense primer corresponding to a nucleotide sequence portion on the 3'-terminal side thereof. An example of such a sense primer or antisense primer may be an oligonucleotide consisting of approximately 10 to 60 nucleotides, the melting temperature (Tm) and the number of nucleotides of which are not drastically changed. An oligonucleotide consisting of approximately 10 to 40 nucleotides is preferable. Moreover, in the present invention, it is also possible to use derivatives of the aforementioned oligonucleotide. For example, a methyl form, a phosphorothioate form or the like of the above oligonucleotide can also be used.

Furthermore, in the present invention, the aforementioned antisense oligonucleotide is introduced into cells to suppress the transcription or translation of the D8 gene, so as to suppress the apoptosis of the cells. That is to say, the present invention provides an apoptosis-inhibiting agent, which comprises an antisense oligonucleotide having a sequence complementary to an oligonucleotide containing at least 10 contiguous nucleotides in the nucleotide sequence of the D8 gene.

A method of introducing an antisense oligonucleotide into cells is the same as the method of introducing a recombinant vector into cells. In addition, a method of detecting the apoptosis of cells is not particularly limited. Examples of such a method may include microscopy, the TUNEL method, the DNA ladder detection method, quantification of the fragmentation rate of DNA, and measurement of cell size distribution.

In the case of microscopy, a change in cell form that is characteristic of apoptosis, such as concentration of the nucleus, condensation of the chromatin, atrophy of the cell organelle, formation of apoptotic corpuscles, or contraction of a cell as a whole, are observed. The TUNEL method is a method of detecting DNA termini cleaved due to apoptosis by labeling with biotin or digoxigenin using terminal deoxynucleotidyl transferase (TdT). The DNA ladder detection method is a method of detecting chromatin DNA fragmentation caused by apoptosis, which comprises extracting DNA from cells and subjecting it to agarose gel electrophoresis, so as to detect fragmentated DNA in the form of a ladder. Quantification of the fragmentation rate of DNA is a method of extracting only fragmentated low molecular weight DNA and quantifying DNA using diphenylamine. Measurement of cell size distribution is a method of measuring an increase in the number of cells with a small size caused by contraction or fragmentation of cells due to apoptosis, using a particle size measurement device such as a Coulter multisizer. By these methods, whether or not cells are involved in apoptosis can be detected.

Using the aforementioned antisense oligonucleotide of the present invention, the transcription and/or translation of the D8 gene is suppressed, so as to inhibit apoptosis, thereby treating diseases, the pathologic conditions of which are associated with promotion of apoptosis (for example, neurodegenerative diseases such as Alzheimer's disease). For example, such an antisense oligonucleotide, together with a suitable carrier with a high affinity for the cell membrane that is used to support incorporation of the above antisense oligonucleotide into cells (for example, liposome, cholesterol, etc.), is administered to the affected area or a body as a whole of a patient by injection or the like, so that it can be incorporated into the cells of the patient to inhibit apoptosis, thereby treating the above diseases. The dosage of an antisense oligonucleotide as an active ingredient is generally approximately between 0.1 μg and 100 mg per kg of body weight per once.

(9) Suppression of Apoptosis Via RNAi

In the present invention, it is also possible to suppress apoptosis by utilizing RNAi instead of the use of the antisense oligonucleotide described in (8) above.

RNAi (RNA interference) is a phenomenon whereby expression of a certain target gene is suppressed when double-stranded RNA (dsRNA) obtained by conversion of a portion of mRNA encoding a part of the target gene is introduced into cells.

That is to say, the present invention provides a double-stranded RNA comprising at least 10 contiguous nucleotides in the nucleotide sequence of RNA that is transcribed from the nucleotide sequence of the apoptosis-inducing gene (D8 gene) of the present invention, or DNA encoding the same. An example of such DNA encoding double-stranded RNA is DNA having an inverted repeat sequence of the apoptosis-inducing gene (D8 gene) or a partial sequence thereof.

By introducing such DNA having an inverted repeat sequence into mammalian cells, the inverted repeat sequence of a target gene can be allowed to express in the cells, and thereby, it becomes possible to suppress the expression of the target gene (D8 gene) due to RNAi effects.

The term "inverted repeat sequence" is used to mean a sequence wherein a target gene sequence is aligned in paralleled with its inverted sequence via a suitable sequence. More specifically, when a target gene has the following double strand consisting of n number of nucleotides:

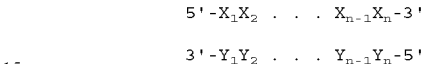

its inverted sequence has the following sequence:

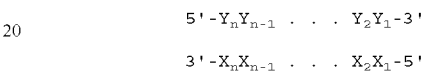

(wherein when a nucleotide represented by X and a nucleotide represented by Y have the same numerical subscript, these nucleotides are complementary to each other).

The inverted repeat sequence is a sequence wherein the two above types of sequences are aligned in parallel via a suitable sequence. It is considered that there are two cases related to such an inverted repeat sequence: a case where the sequence of a target gene is located upstream of the inverted sequence; and a case where the inverted sequence is located upstream of the sequence of a target gene. The inverted repeat sequences of both the above cases may be used in the present invention, but preferably, the inverted sequence is located upstream of the sequence of a target gene.

A sequence existing between the target gene sequence and the inverted sequence thereof is a region which forms a hairpin loop when it is transcribed into RNA. The length of this region is not particularly limited, as long as it can form a hairpin loop. It is generally between 0 bp and 700 bp, preferably approximately between 0 bp and 300 bp, and more preferably approximately between 0 bp and 100 bp. Restriction sites may also exist in this sequence.

In the present invention, the inverted repeat sequence of a target gene can be allowed to express in mammalian cells by incorporating the inverted repeat sequence of a target gene downstream of a promoter sequence capable of functioning in mammals. A promoter sequence used in the present invention is not particularly limited, as long as it is capable of functioning in mammals.

Moreover, the present invention provides an apoptosis-inhibiting agent comprising the aforementioned double-stranded RNA or DNA. Using the aforementioned double-stranded RNA or DNA, the transcription and/or translation of the D8 gene is suppressed, so as to inhibit apoptosis, thereby treating diseases, the pathologic conditions of which are associated with promotion of apoptosis (for example, neurodegenerative diseases such as Alzheimer's disease). For example, the aforementioned double-stranded RNA or DNA, together with a suitable carrier with a high affinity for the cell membrane that is used to support incorporation of the above double-stranded RNA or DNA into cells (for example, liposome, cholesterol, etc.), is administered to the affected area or body as a whole of a patient by injection or the like, so that it can be incorporated into the cells of the patient to inhibit apoptosis, thereby treating the above diseases. The dosage of such double-stranded RNA or DNA as an active ingredient is generally approximately between 0.1 µg and 10 mg per kg of body weight per once.

(10) Control of Apoptosis Using the Apoptosis-Inducing Protein of the Present Invention As stated in the above sections: (7) Antibody against the apoptosis-inducing protein; (8) Oligonucleotide and antisense oligonucleotide; and (9) Suppression of apoptosis via RNAi, it is possible to suppress apoptosis by inhibiting the expression of the apoptosis-inducing protein of the present invention and/or the functions thereof. Methods for suppressing apoptosis by inhibiting the expression of the apoptosis-inducing protein of the present invention and/or the functions thereof are all included in the scope of the present invention.

Specific examples of a method for suppressing apoptosis may include a method for treating diseases associated with promotion of apoptosis and a method for suppressing cell death due to apoptosis. For example, several methods are described in the following sections: (a) Production of useful protein; and (b) Transplanted cells and transplanted organs.

(a) Production of Useful Protein

There are some cases where cell strains producing useful proteins, such as antibody-generating cell strains (hybridomas) or viral vector-generating cell strains, may be led to cell death due to the cytotoxicity of proteins produced during a long-term culture. These cell strains can more efficiently produce proteins when the serum is eliminated from the culture solution. However, such cell strains are problematic in that cell death is induced in the absence of such serum. It has been known that such cell death is caused by apoptosis in many cases. Accordingly, the production efficiency of useful proteins can be increased by suppressing apoptosis by the method of the present invention.

(b) Transplanted Cells and Transplanted Organs

For the treatment of Parkinson's disease, a method of transplanting neurocytes or dopamine-producing cells of dead fetuses is applied into the brain of a patient. A cell transplantation therapy, which comprises introducing autogenous or allogenic cells into a patient, such as the ex vivo method applied to blood transfusion, bone marrow transplantation, or gene therapy, is also carried out. In general, transplanted cells are led to cell death due to apoptosis, and it is difficult to maintain such transplanted cells for a long period of time. Accordingly, suppression of apoptosis by the method of the present invention brings on good results in organ transplantation or cell transplantation therapy.

Moreover, an apoptosis-inhibiting agent containing a substance that inhibits the expression of the apoptosis-inducing protein of the present invention and/or the functions thereof is also included in the scope of the present invention. Specific examples of a substance that inhibits the expression of the apoptosis-inducing protein of the present invention and/or the functions thereof may include: the antibody described in (7) above, the antisense oligonucleotide described in (8) above, and the double-stranded RNA or DNA encoding the same described in (9) above in the present specification. However, examples are not limited thereto.

Furthermore, in contrast to the above descriptions, a method for promoting apoptosis by increasing the expression of the apoptosis-inducing protein of the present invention and/or the functions thereof is also included in the scope of the present invention. Likewise, an apoptosis-promoting agent comprising a substance that increases the expression of the apoptosis-inducing protein of the present invention and/or the functions thereof is also included in the scope of the present invention.

Examples of a method for increasing the expression of the apoptosis-inducing protein of the present invention and/or the functions thereof may include a method of introducing a gene encoding the apoptosis-inducing protein of the present invention into cells and a method of introducing a factor acting on the promoter region of the above gene thereby increasing the expression thereof or a gene encoding the factor into cells.

The presence or absence of suppression or promotion of apoptosis and the degree thereof can be detected by the methods as described above in the present specification, such as microscopy, the TUNEL method, the DNA ladder detection method, quantification of the fragmentation rate of DNA, or measurement of cell size distribution.

(11) Method for Screening Apoptosis-Controlling Substance

Using, as an indicator, a change in the expression of the apoptosis-inducing protein (D8) identified by the present invention and/or in the functions thereof, a substance for inhibiting or promoting apoptosis can be screened. As an example of such screening, cells having a gene encoding the apoptosis-inducing protein of the present invention are cultured together with TGF-β in the presence or absence of a test substance, and thereafter, a substance for inhibiting or promoting apoptosis can be screened, using, as an indicator, a change in the expression of the above apoptosis-inducing protein and/or in the functions thereof, which depends on the presence of the absence of a test substance.

The expression level of the apoptosis-inducing protein can be measured at the mRNA level by a common method such as Northern blotting or RT-PCR described in (8) above in the present specification. On the other hand, the expression level thereof at the protein level can be measured by a common immune assay, such as Western blotting or ELISA, using the antibody described in (7) above in the present specification. Specifically, such measurement of the expression level can be carried out by common methods that are known to persons skilled in the art, such as the methods described in Molecular Cloning $2^{nd}$ Ed., or in Current Protocols in Molecular Biology.

Moreover, a change in the functions of the apoptosis-inducing protein can be analyzed by examining whether or not apoptosis induction is inhibited or promoted, or the degree thereof. The aforementioned measurement of apoptosis induction can be carried out by microscopy, the TUNEL method, the DNA ladder detection method, quantification of the fragmentation rate of DNA, measurement of cell size distribution, or the like, as described above in the present specification.

Any given substance can be used as a test substance subjected to the screening method of the present invention. The type of a test substance is not particularly limited. A test substance may be a low molecular weight synthetic compound, a compound existing in an extract from a nature product, or a synthetic peptide. Otherwise, such a test substance may also be a compound library, a phage display library, or a combinatorial library. Such a test substance is preferably a low molecular weight compound, and a compound library of low molecular weight compounds is more preferable. Construction of a compound library is known to persons skilled in the art. Also, a commercially available compound library can be used.

It has been known that apoptosis is associated with not only a normal physiological process, but also the onset of serious disease such as cancers, autoimmune diseases (for example, systemic lupus erythematosus, chronic rheumatoid arthritis, multiple sclerosis, etc.), or neurodegenerative diseases. For example, it is considered that malignant degeneration of cancer cells is caused by the phenomenon whereby an apoptotic process in cancer cells is inhibited and cells to be intrinsically killed continuously proliferate (Harris, C. C., (1996) J. Natl. Cancer Instit., 88, 1442-1445). Autoimmune disease is developed by the phenomenon whereby immunocytes reacting with autoantigens that should have intrinsically been eliminated due to apoptosis during the development process are not eliminated due to the abnormity of apoptosis control (Rieux-Laucat, F. et al., (1995) Science, 268, 1347-1349). It is considered that neurodegenerative disease (for example, Alzheimer's disease, Parkinson's disease, amyotrophic lateral sclerosis, Huntington's chorea, etc.) is caused by abnormal accentuation of apoptosis (Wolozin B. et al., (1996) Science, 274, 1710-1713).

Accordingly, the aforementioned apoptosis-inhibiting substance of the present invention is considered to be particularly effective as an agent for treating neurodegenerative diseases. In addition, an apoptosis-promoting substance is considered to be particularly effective as an agent for treating various types of cancers or autoimmune diseases such as rheumatism.

An agent for treating diseases associated with apoptosis, which comprises, as an active ingredient, the aforementioned apoptosis-inhibiting substance or apoptosis-promoting substance of the present invention, can be locally or systemically administered via an oral or parenteral route. Examples of a parenteral administration method may include intravenous injection such as drip infusion, intramuscular injection, intraperitoneal injection, and subcutaneous injection. Such an administration method can appropriately be selected depending on the age or symptoms of a patient. The dosage is different depending on the age of a patient, an administration route, and the number of administrations. Persons skilled in the art can appropriately select the dosage.

An example of a dosage form suitable for parenteral administration may be an agent which contains additives such as a stabilizer, a buffer agent, a preservative, or an isotonizing agent. Such an agent may further contain a pharmacologically acceptable carrier or additive. Examples of such a carrier and an additive may include water, an organic solvent, a polymer (collagen, polyvinyl alcohol, etc.), stearic acid, human serum albumin (HSA), mannitol, sorbitol, lactose, and a surfactant, but examples are not limited thereto.

All of the contents as disclosed in the specification and/or drawings of Japanese Patent Application No. 2003-32036, which is the priority document of the present application, are incorporated herein by reference as a part of disclosure of the present specification.

The present invention will be more specifically described in the following examples. However, the scope of the present invention is not limited by the examples.

EXAMPLES

Example 1

Screening of TGF-β Target Gene 10 ml of Opti MEM medium (0.02% FBS) was added to $2 \times 10^6$ A549 cells. 24 hours later, TGF-β1 (R & D) was added thereto to a concentration of 1 ng/ml, and the obtained mixture was left for 1 hour. RNeasy Mini kit (QIAGEN) was used to recover total RNA. Oligotex-dT30 <super> (JRS) was used to prepare poly(A)+RNA. Thereafter, subtraction was carried out by subtracting cDNA produced from poly(A)+RNA of A549 cells that had not been treated with TGF-β1, from cDNA produced from poly(A)+RNA of A549 cells that had been treated with TGF-β1 for 1 hour. Such subtraction was carried out in accordance with the protocols provided with CLONTECH PCR-Select™ cDNA Subtraction Kit (CLONTECH). A library obtained by the subtraction was subjected to PCR, so as to produce a microarray. For such a microarray, cDNA obtained by labeling, with Cy5, poly(A)+RNA recovered from A549 cells that had been treated with TGF-β1 for 1 hour, and cDNA obtained by labeling, with Cy3, poly(A)+RNA recovered from A549 cells that had not been treated with TGF-β1, were used as probes. A gene whose expression is changed by TGF-β1 was analyzed by hybridization of both probes with a single microarray. As a result, D8 was identified as a novel gene, the expression level of which is significantly different by TGF-β1.

The nucleotide sequence of DNA of the full-length D8 was predicted by ligating the nucleotide sequences of DNAs of EST clones, using BLAST from NCBI. A D8FW primer: 5'-TATAGAATTCATGCCCAGCTCGCTGTTCGC-3' (SEQ ID NO: 3) and a D8RV primer: 5'-TATAGTCGACTTAA-GAAAAGATGCGGATGG-3' (SEQ ID NO: 4) were produced from the predicted nucleotide sequence of DNA of the full-length D8, and PCR was then performed using a human testis library as a template, so as to recover an amplified product, thereby determining the nucleotide sequence of DNA of the full-length D8. As a result, it was found that D8 has a full length consisting of 1,710 nucleotides (SEQ ID NO: 1), and also consisting of 569 amino acids (SEQ ID NO: 2), and that D8 has two KH domains functioning as RNA-binding motifs on the N-terminal side thereof, a Ring finger domain functioning as ubiquitin ligase E3 on the C-terminal side thereof, and a region, the functions of which remain unknown but which is serine-rich, in the center thereof (FIG. 1).

Figure 2:
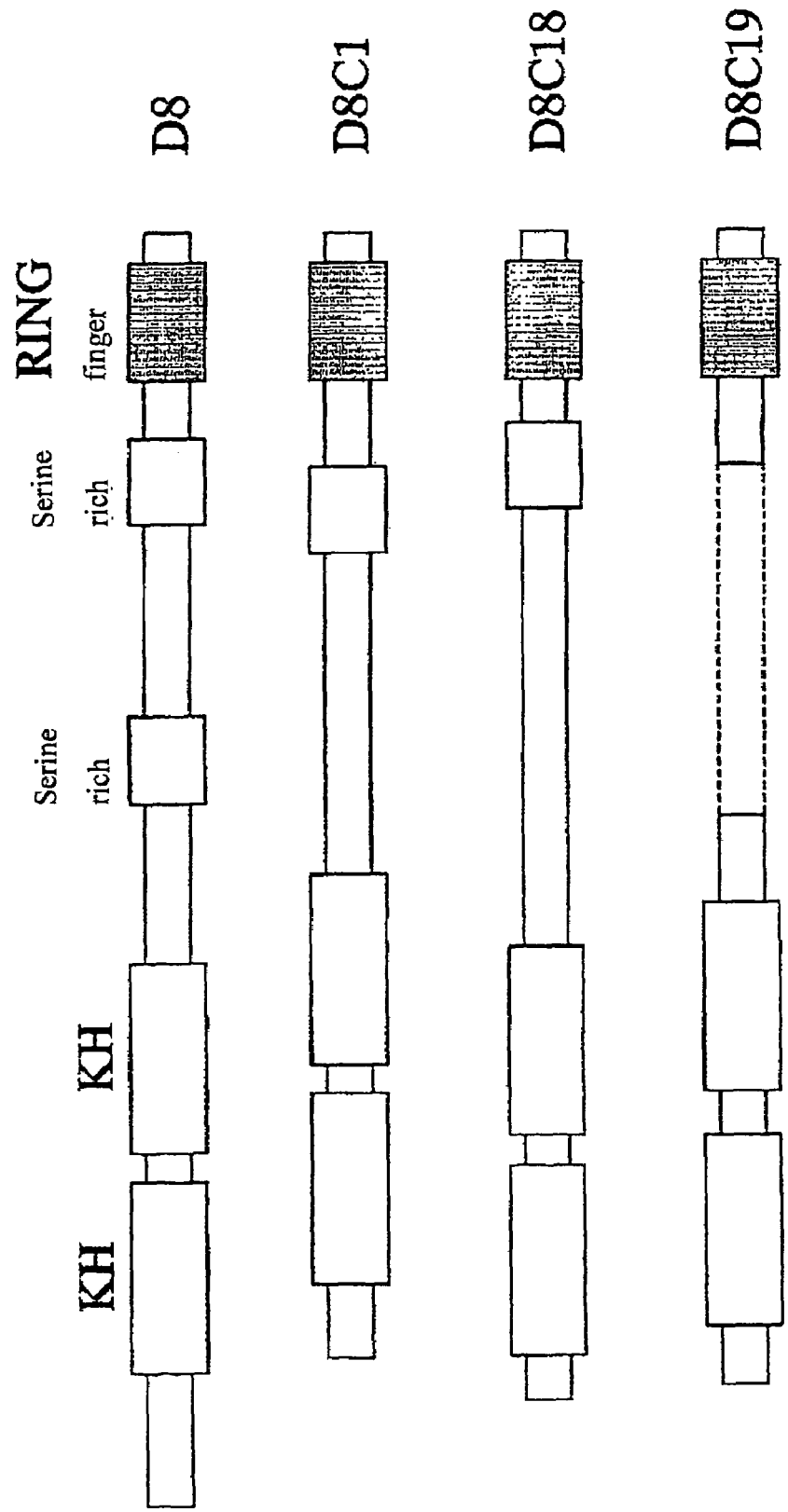
FIG. 2 shows a structure of the D8 family (human).

The structure of a D8 family is shown in FIGS. 1 and 2. As a result of search using BLAST from NCBI, it was found that D8 homologs exist in nematodes and drosophila. Thus, it is considered that D8 is an important gene that has been conserved during the evolution from nematodes to humans. Moreover, humans have 3 types of D8-related proteins, which have high homology with D8, and whose domain structure has been conserved. These D8-related proteins constitute a D8 family.

The alignments of two KH domains and a Ring finger domain of the D8 family are shown in FIG. 3. Since both the KH domains and the Ring finger domain have been conserved at an extremely high degree, it is considered that the D8 family has the same functions.

Example 2

Induction of Expression of D8 by TGF-β

Figure 4:
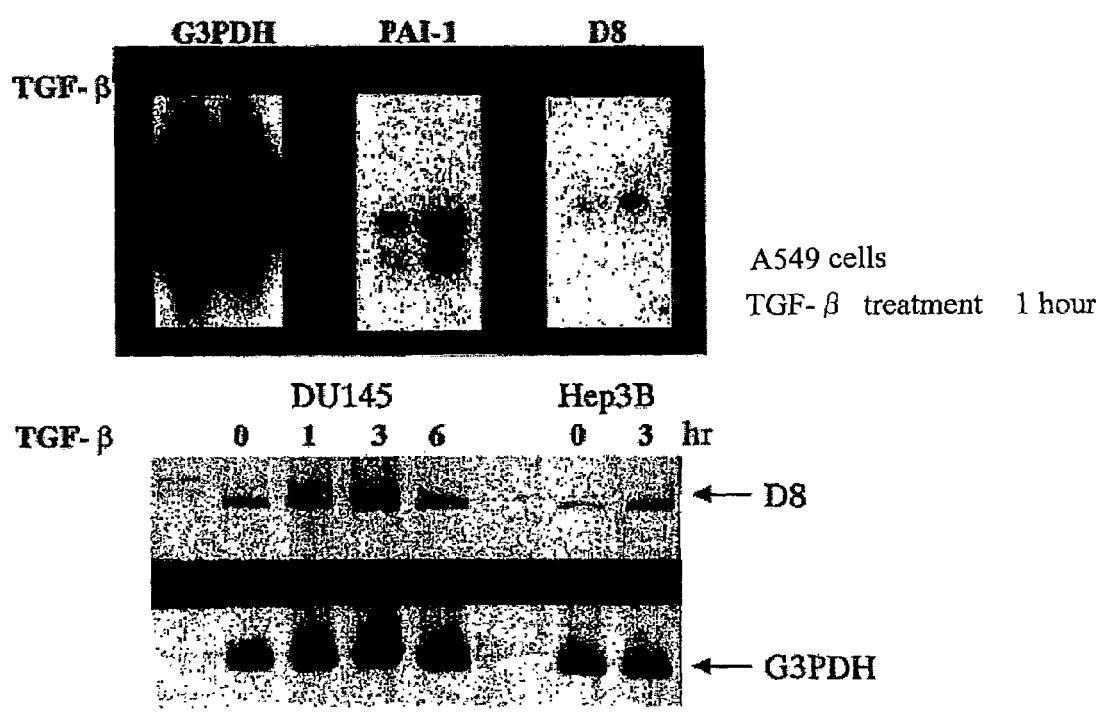
FIG. 4 shows the results of induction of the expression of D8 by TGF-$\beta$1.

(1) 10 ml of Opti MEM medium (0.02% FBS) was added to $2 \times 10^6$ A549 cells. 24 hours later, TGF-β1 (R & D) was added thereto to a concentration of 1 ng/ml, and the obtained mixture was left for 1 hour. RNeasy Mini kit (QIAGEN) was used to recover total RNA. Oligotex-dT30 <super> (JRS) was used to prepare poly(A)+RNA. Northern Hybridization was carried out using 2 μg each of poly(A)+RNA recovered from A549 cells that had been treated with TGF-β1 for 1 hour and untreated A549 cells, and using ORF of D8 as a probe. G3PDH was used as a loading control, and PAI-1 was used as a positive control regarding TGF-β1 response. The results are shown in the upper case of FIG. 4. As is clear from the results, it was shown that the expression of D8 was induced by TGF-β1.

(2) Total RNA was recovered from each of DU145 cells and Hep3B cells by the same method as that described in (1)

above. cDNA was synthesized from 1 μg of total RNA using Advantage RT-for-PCR Kit (CLONTECH). PCR was carried out on G3PDH for 25 cycles, and on D8 for 30 cycles. The results are shown in the lower case of FIG. 4. As is clear from the results, it was showed that the expression of D8 was induced by TGF-β1 also in the DU145 cells and in the Hep3B cells.

Example 3

Activation of D8 Promoter by TGF-β

(1) D8 Reporter Construction

A reporter was produced by introducing a luciferase gene downstream of a DNA fragment located upstream of the ORF of D8. A human genomic DNA fragment, which was predicted to contain a D8 promoter region, was recovered by PCR using BAC clone homo sapiens chromosome 15, clone RP11-597K23, as a template. The recovered DNA fragment was then inserted into the XhoI-NcoI site of a pGL3 promoter vector (Promega) (the left view of FIG. 5).

(2) Effects of TGF-β1 on D8 Reporter Construction

A D8 reporter construction was introduced into $1 \times 10^5$ Hep3B cells using Effectene™ Transfection Reagent (QIAGEN). A pGL3 basic vector was used as a control, 3TPLux was used as a positive control, and pRLTK was used as an internal control. For the gene transfer, 0.1 μg of a reporter, 0.1 μg of an expression vector, and 0.001 μg of an internal control were used. 18 hours after introduction of the reporter, TGF-β (R & D) was added thereto to a concentration of 10 ng/ml. Thereafter, the obtained mixture was left for 24 hours. A Dual-Luciferase Reporter Assay system (Promega) was used to measure luciferase. The results are shown in the right view of FIG. 5. As is clear from the results, luciferase activity was decreased, as the length of the existing promoter was reduced. These results suggest that TGF-β1 acts on the D8 promoter, so as to activate it.

Example 4

Colony Formation Assay

Each of 2 μg of pcDNA and 2 μg of pcDNA-FlagD8 was introduced into $1 \times 10^6$ Hep3B cells, using Effectene™ Transfection Reagent (QIAGEN). 24 hours later, the cells were recovered by treatment with trypsin, and they were then diluted and placed in 3 pieces of 10-cm dishes. 24 hours after the dilution, geneticin was added thereto to a concentration of 200 μg/ml. The mixture was then left for 14 days. Thereafter, the reaction product was stained with crystal violet. The results are shown in the left view of FIG. 6. The results obtained by counting the number of colonies are shown in the right view of FIG. 6. As is clear from these results, cell proliferation was suppressed by introduction of the D8 gene.

Example 5

Effects of D8 on Cell Death (Apoptosis) That is Induced by TGF-β

Each of pcDNA and pcDNA-FLAGD8, together with a LacZ expression plasmid, was introduced into $1 \times 10^4$ Hep3B cells, using Effectene™ Transfection Reagent (QIAGEN). For the gene transfer, 0.025 μg of an expression vector and 0.0125 μg of a LacZ expression plasmid were used. 18 hours after the gene transfer, the medium was changed into DMEM medium (0% FBS), and TGF-β1 was then added thereto to a concentration of 5 ng/ml. The mixture was cultured for 24 hours. 24 hours after addition of TGF-β1, the cells were fixed with 1% glutaraldehyde and then stained with X-gal. In the present study, all the cells on a well that were stained to blue were counted. The cells stained to blue were defined as surviving cells, and cells into which an empty vector had been introduced were defined as controls.

Figure 7:
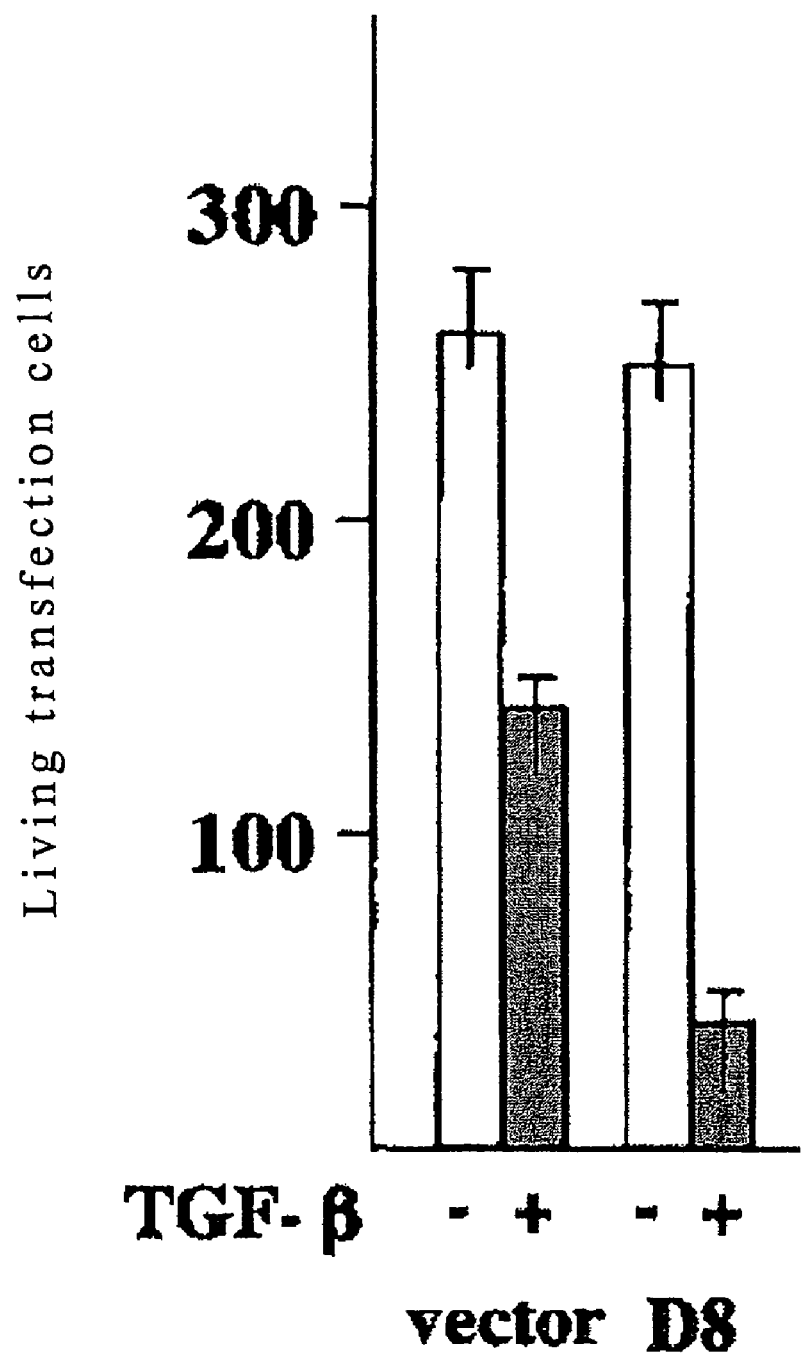
FIG. 7 shows the results of the measurement of the effects of D8 on cell death (apoptosis) inducted by TGF-$\beta$1.

As is clear from the results shown in FIG. 7, it was shown that cell death (apoptosis) induced by TGF-β1 was promoted by gene transfer of D8.

Example 6

Effects of D8 Deletion Mutant on Apoptosis That is Induced by TGF-β

(1) Construction of D8 Deletion Mutants

Figure 8:
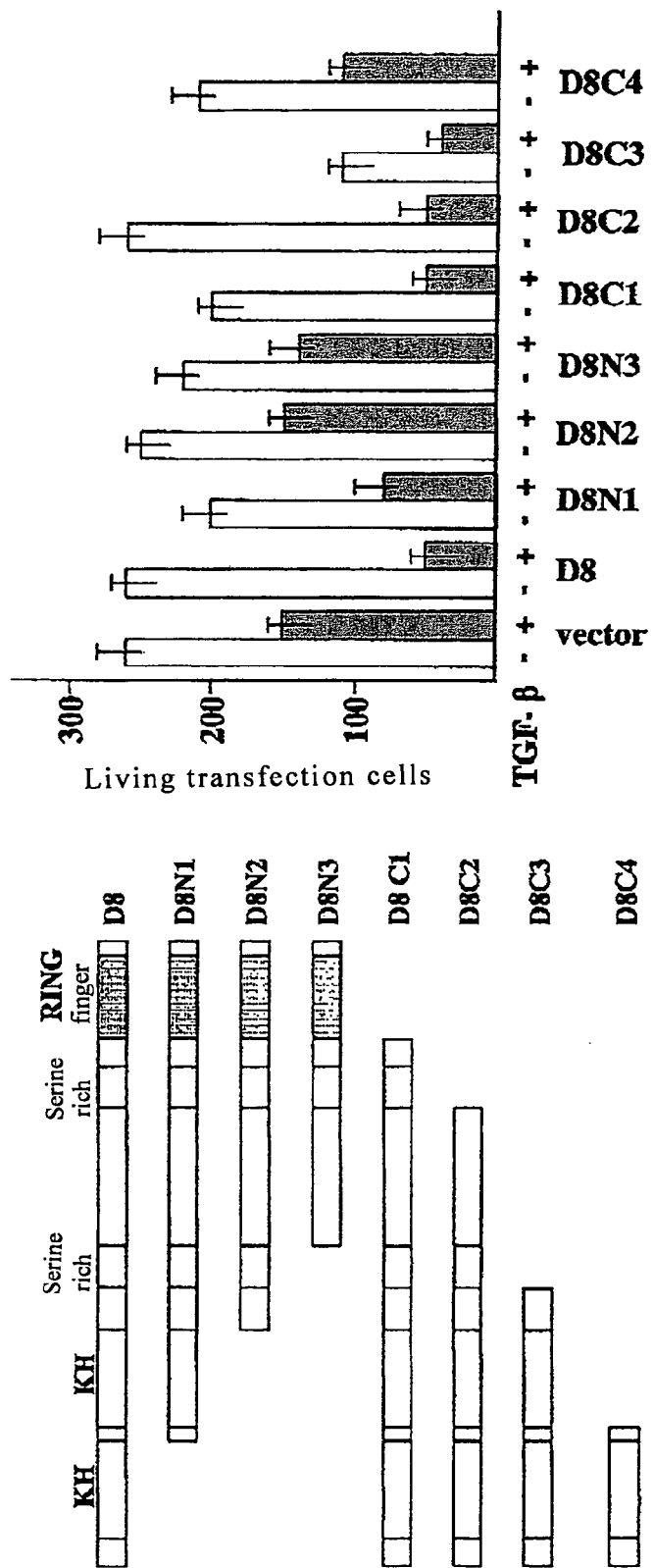
FIG. 8 shows the effects of a D8 deletion mutant on apoptosis induced by TGF-$\beta$1.

Deletion mutants shown in the left view of FIG. 8 were produced by PCR. The details of the deletion mutants shown in the left view of FIG. 8 are as follows:

D8N1: an amino acid sequence corresponding to a portion from position 136 to position 569 of the amino acid sequence of D8 (SEQ ID NO: 27)

D8N2: an amino acid sequence corresponding to a portion from position 230 to position 569 of the amino acid sequence of D8 (SEQ ID NO: 28)

D8N3: an amino acid sequence corresponding to a portion from position 408 to position 569 of the amino acid sequence of D8 (SEQ ID NO: 29)

D8C1: an amino acid sequence corresponding to a portion from position 1 to position 510 of the amino acid sequence of D8 (SEQ ID NO: 30)

D8C2: an amino acid sequence corresponding to a portion from position 1 to position 492 of the amino acid sequence of D8 (SEQ ID NO: 31)

D8C3: an amino acid sequence corresponding to a portion from position 1 to position 392 of the amino acid sequence of D8 (SEQ ID NO: 32)

D8C4: an amino acid sequence corresponding to a portion from position 1 to position 164 of the amino acid sequence of D8 (SEQ ID NO: 33)

(2) Effects of D8 Deletion Mutant on Apoptosis

Each of the D8 deletion mutants, together with a LacZ expression plasmid, was introduced into $1 \times 10^4$ Hep3B cells, using Effectene™ Transfection Reagent (QIAGEN). For the gene transfer, 0.05 μg of an expression vector and 0.125 μg of a LacZ expression plasmid were used. 18 hours after the gene transfer, the medium was changed into DMEM medium (0% FBS), and TGF-β1 was then added thereto to a concentration of 5 ng/ml. The mixture was cultured for 24 hours. 24 hours after addition of TGF-β1, the cells were fixed with 1% glutaraldehyde and then stained with X-gal. The results obtained by measurement of the number of surviving cells are shown in the right view of FIG. 8. As is clear from the results, it was suggested that the KH domains (RNA-binding domains) existing on the N-terminal side of D8 are essential for induction of apoptosis by TGF-β1, but that the Ring finger domain existing on the C-terminal side thereof is not essential for such induction of apoptosis.

Example 7

RNAi Effects of D8 on Apoptosis That is Induced by TGF-β

(1) Suppression of Expression of D8 Due to RNAi Effects of D8

As plasmids for expressing RNAi of D8, synthetic oligonucleotides (D8iF1 and D8iR1) were produced based on the nucleotide sequence of DNA portion from position 216 to position 236 of D8. For annealing, 1 μl of D8iF1 (100 pmol) and 1 μl of D8iR1 (100 pmol) were added to 48 μl of an annealing buffer [100 mM potassium acetate, 30 mM HEPES-KOH (pH7.4), and 2 mM Mg acetate], followed by treating at 95° C. for 4 minutes and then at 70° C. for 10 minutes. Thereafter, the reaction product was left at room temperature for 30 minutes. Thereafter, the annealed synthetic oligonucleotides were inserted into the BseRI-BamHI site of a pSHAG vector (pSHAG-D8i).

Synthetic Oligonucleotides

```
D8iF1:                                           (SEQ ID NO: 5)
5'-acatgctcagaactgggtactggcacgcgaagcttggcgtgccagta
cccagttctgagcatgtcgctttttt-3'

D8iR1:                                           (SEQ ID NO: 6)
5'-gatcaaaaaagcgacatgctcagaactgggtactggcacgccaagct
tcgcgtgccagtacccagttctgagcatgtcg-3'
```

Figure 9:
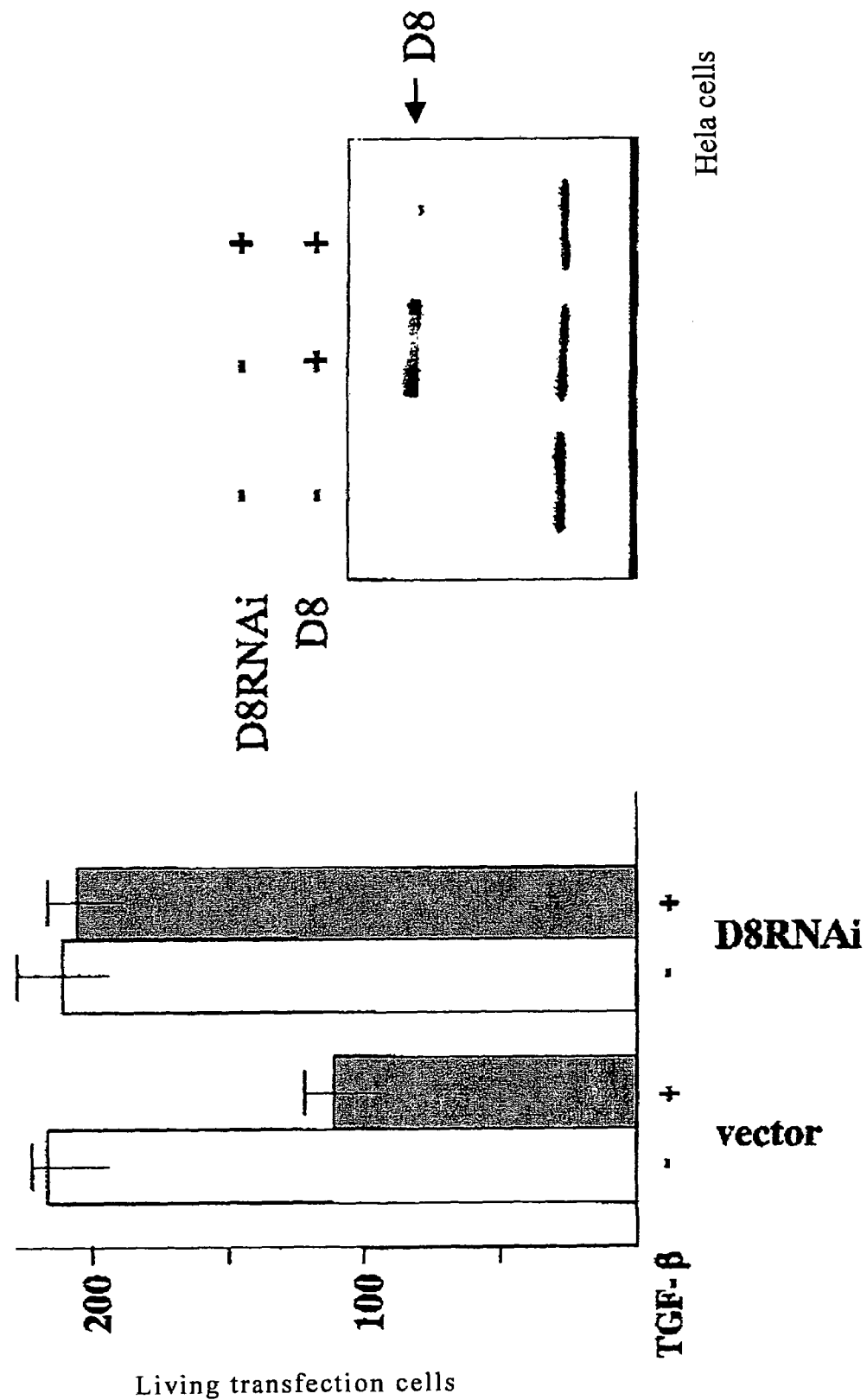
FIG. 9 shows the results of the measurement of the RNAi effects of D8 on apoptosis induced by TGF-$\beta$1.

Each of EGFP-D8 and pSHAG-D8i was introduced into 1×10⁶ Hela cells, using Effectene™ Transfection Reagent (QIAGEN). For the gene transfer, 1 μg of an expression vector and 1 μg of an RNAi expression vector were used. 24 hours after the gene transfer, the cells were dissolved in a dissolving buffer [50 mM Tris-HCl (pH7.4), 150 mM NaCl, and 1% Triton X-100], and 1 μg of anti-AFP mAB 3E6 (QUANTUM) was then added thereto. The obtained mixture was left for 1 hour. Thereafter, 50 μl of protein G-sepharose (obtained by suspension of gel in buffer at a ratio of 1:1) was added thereto, and the obtained mixture was left for 1 hour. The reaction product was then washed with a washing buffer [50 mM Tris-HCl (pH7.4), 150 mM NaCl, and 0.05% Triton X-100], and the thus obtained product was used as a sample for immunoprecipitation. The immune precipitate was electrophoresed using 10% acrylamide gel. Western blotting was carried out, using living Colors A.v. Peptide Antibody (CLONTEC) [1 μg/ml] as a primary antibody, and using Anti-Rabbit IgG (Fc) AP Conjugate (Promega) [0.2 μg/ml] as a secondary antibody. The results are shown in the right view of FIG. 9. The results show that the expression of D8 is suppressed due to RNAi effects on D8.

(2) Suppression of Apoptosis Due to RNAi Effects of D8 pSHAG-D8i for expressing RNAi of D8, together with a LacZ expression vector, was introduced into 1×10⁴ Hep3B cells, using Effectene™ Transfection Reagent (QIAGEN). For the gene transfer, 0.05 μg of an RNAi expression vector and 0.0125 μg of a LacZ expression plasmid were used. 18 hours after the gene transfer, the medium was changed into DMEM medium (0% FBS), and TGF-β1 was then added thereto to a concentration of 5 ng/ml. The mixture was cultured for 24 hours. 24 hours after addition of TGF-β1, the cells were fixed with 1% glutaraldehyde and then stained with X-gal. The results obtained by measurement of the number of surviving cells are shown in the left view of FIG. 9. It was shown that apoptosis induced by TGF-β1 was suppressed due to RNAi effects of D8.

Example 8

In Vitro Ubiquitination Assay of D8

Figure 10:
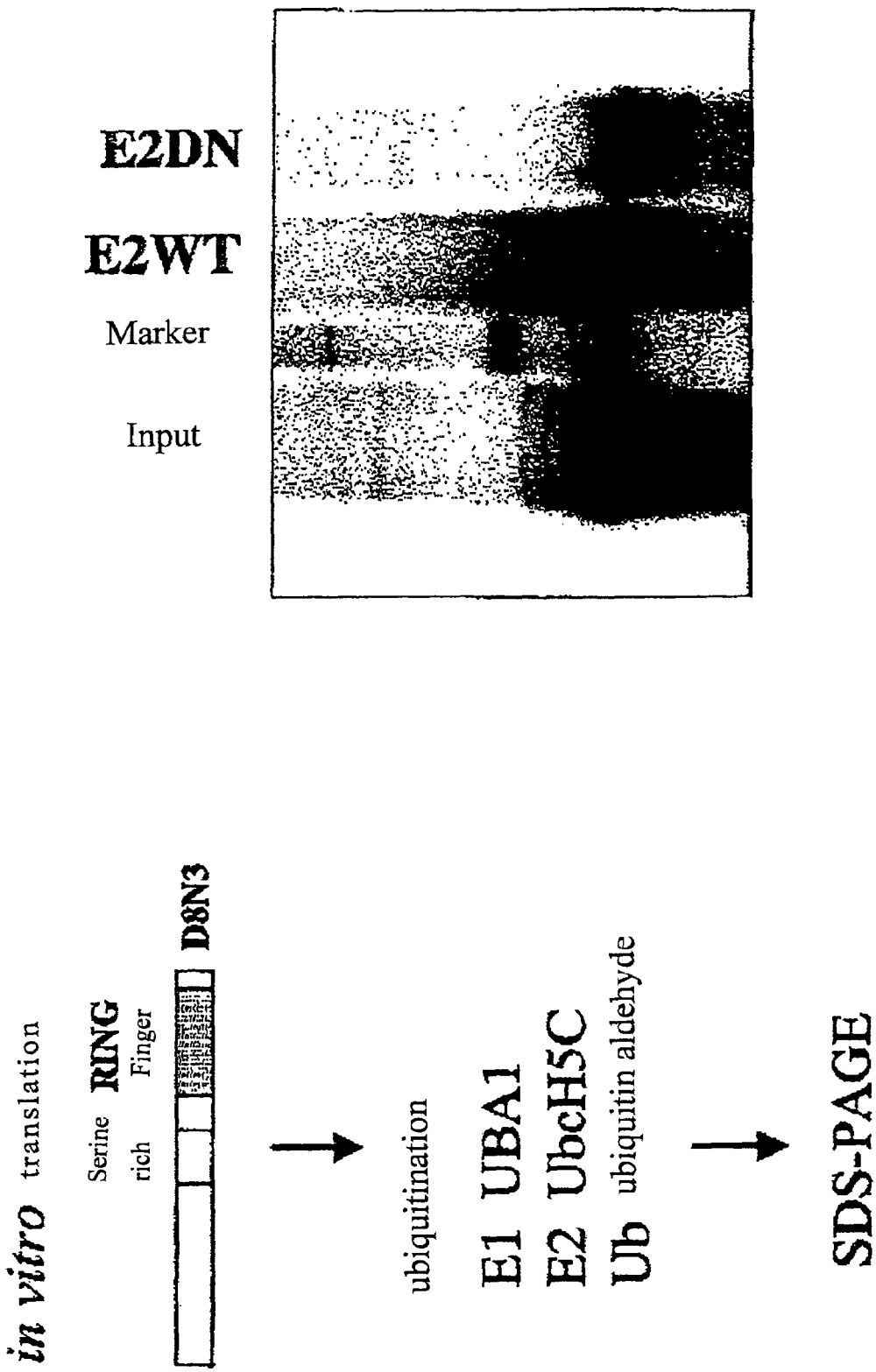
FIG. 10 shows the results of the in vitro ubiquitination assay of D8.

A $^{35}$S-labelesd D8N3 protein was synthesized by in vitro translation using TNT Quick Coupled Transcription/Translation System (Promega). Subsequently, 0.1 μg of the $^{35}$S-labeled D8N3 protein, 0.02 μg of E1 (UBA1), and 0.02 μg of E2 (a wild type or a dominant negative type of UbcHC) were added to an in vitro ubiquitination buffer [50 mM Tris-HCl (pH7.4), 0.2 mM ATP, 0.5 mM MgCl$_2$, 0.1 mM DTT, 1 mM creatine phosphate, 15 units of creatine phosphokinase, 5 μM LLNL, and 3 μM Ubiquitin aldehyde]. The mixture was then left at 30° C. for 90 minutes. Thereafter, SDS-PAGE was carried out using acrylamide gel [PAG Mini DAIICHI 2/15 (13W) (Daiichi Chemicals)]. The results are shown in FIG. 10. The results show that D8 functions as ubiquitin ligase E3.

INDUSTRIAL APPLICABILITY

According to the present invention, a novel apoptosis-inducing gene has been identified. Using the gene of the present invention, the expression of the gene of the present invention can be detected in various tissues, or an apoptosis-inducing protein can be produced by genetic engineering. In addition, using the gene of the present invention, the diagnosis of diseases associated with apoptosis and the screening of an apoptosis-inhibiting agent or apoptosis-promoting agent can be carried out. Moreover, the gene of the present invention is extremely useful for the development of a gene therapy directed towards suppression of apoptosis and a method for preventing or treating diseases using an antisense oligonucleotide.

The invention claimed is:

1. An isolated and purified apoptosis-inducing protein of any one of the following (a) and (b):
   (a) a protein having the amino acid sequence shown in SEQ ID NO: 2 of the sequence listing; and
   (b) a protein having sequence identity of 95% or more with the amino acid sequence shown in SEQ ID NO: 2 of the sequence listing, and having apoptosis-inducing activity.

2. A method for screening a substance that inhibits or promotes apoptosis, using a change in the expression of the apoptosis-inducing protein of claim 1 as an indicator.

3. The method according to claim 2, which comprises culturing cells having a gene encoding said apoptosis-inducing protein, together with TGF-β, in the presence or absence of a test substance, and screening the above substance using, as an indicator, a change in the expression of said apoptosis-inducing protein, which depends on the presence or absence of the test substance.

* * * * *